US010702653B2

(12) United States Patent
Ogawa et al.

(10) Patent No.: US 10,702,653 B2
(45) Date of Patent: Jul. 7, 2020

(54) SYRINGE HOLDER AND PHARMACEUTICAL LIQUID ADMINISTRATION SET

(71) Applicant: TERUMO KABUSHIKI KAISHA, Tokyo (JP)

(72) Inventors: Junichi Ogawa, Yamanashi (JP); Yoichiro Iwase, Yamanashi (JP); Kazunori Koiwai, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 165 days.

(21) Appl. No.: 15/712,364

(22) Filed: Sep. 22, 2017

(65) Prior Publication Data

US 2018/0008776 A1 Jan. 11, 2018

Related U.S. Application Data

(63) Continuation of application No. PCT/JP2016/059316, filed on Mar. 24, 2016.

(30) Foreign Application Priority Data

Mar. 24, 2015 (JP) .................. 2015-061646
Mar. 24, 2015 (JP) .................. 2015-061647

(51) Int. Cl.
*A61M 5/24* (2006.01)
*A61M 5/28* (2006.01)
(Continued)

(52) U.S. Cl.
CPC .................. *A61M 5/24* (2013.01); *A61J 1/16* (2013.01); *A61M 5/28* (2013.01); *A61M 5/31* (2013.01); *A61M 5/3137* (2013.01); *A61M 5/326* (2013.01); *A61M 5/344* (2013.01); *A61M 5/3129* (2013.01); *A61M 5/32* (2013.01); *A61M 5/3202* (2013.01); *A61M 5/3271* (2013.01); *A61M 5/347* (2013.01); *A61M 2005/2488* (2013.01); *A61M 2005/3104* (2013.01); *A61M 2005/3139* (2013.01);
(Continued)

(58) Field of Classification Search
CPC .................................. A61M 5/24; A61M 5/28
See application file for complete search history.

(56) References Cited

U.S. PATENT DOCUMENTS

| 2005/0165353 | A1* | 7/2005 | Pessin ................ A61M 5/3272 604/110 |
| 2006/0095010 | A1* | 5/2006 | Westbye ............... A61M 5/326 604/197 |
| 2009/0105663 | A1 | 4/2009 | Brand et al. |

FOREIGN PATENT DOCUMENTS

| JP | 2001-518366 | 10/2001 |
| JP | 2003-339865 | 12/2003 |

OTHER PUBLICATIONS

International Search Report issued in International Patent Application No. PCT/JP2016/059316 dated May 24, 2016.

* cited by examiner

*Primary Examiner* — Laura A Bouchelle
(74) *Attorney, Agent, or Firm* — Foley & Lardner LLP

(57) ABSTRACT

A syringe holder includes: a barrel body that holds a syringe; a holder opening; deformation promoting portions; and radial movement-restricting portions. The radial movement-restricting portions are provided close to the deformation promoting portions. Being brought into contact with first portions, the radial movement-restricting portions restrict the syringe from moving in a radial direction with respect to the barrel body.

20 Claims, 17 Drawing Sheets

(51) Int. Cl.
*A61M 5/31* (2006.01)
*A61M 5/34* (2006.01)
*A61M 5/32* (2006.01)
*A61J 1/16* (2006.01)
*A61M 5/50* (2006.01)

(52) U.S. Cl.
CPC ............... *A61M 2005/3247* (2013.01); *A61M 2005/3261* (2013.01); *A61M 2005/3264* (2013.01); *A61M 2005/5033* (2013.01)

SYRINGE HOLDER AND PHARMACEUTICAL LIQUID ADMINISTRATION SET

CROSS-REFERENCE TO RELATED APPLICATIONS

The present application is a bypass continuation of PCT Application No. PCT/JP2016/059316, filed on Mar. 24, 2016, which claims priority to Japanese Application No. 2015-061646, filed on Mar. 24, 2015 and Japanese Application No. 2015-061647, filed on Mar. 24, 2015. The contents of these application are hereby incorporated by reference in their entireties.

BACKGROUND

The present disclosure relates to a syringe holder configured to hold a syringe having a distal end portion configured to be attached via a screw attachment with an administration component to administer a pharmaceutical liquid, and to a pharmaceutical liquid administration set provided with this syringe holder.

In recent years, a prefilled syringe (pharmaceutical liquid administration device), that is, a syringe prefilled with a pharmaceutical liquid, has come into popular use. Using such a prefilled syringe requires no process to draw a pharmaceutical liquid from a vial into the syringe when administering the pharmaceutical liquid, which shortens the time required for administration.

A typical prefilled syringe includes a body section and a plunger. When administering a pharmaceutical liquid into a body with the prefilled syringe, the plunger is operated and the pharmaceutical liquid filled in a liquid chamber of the body section is discharged into the body through an injection needle coupled to a distal end of the body section.

When administering a small amount of pharmaceutical liquid, a small prefilled syringe with a small liquid chamber is used. For example, perpendicularly puncturing the skin with an injection needle to administer a pharmaceutical liquid requires a large injection pressure, and inhibiting leakage of the pharmaceutical liquid requires the prefilled syringe being pressed against the skin strongly with a stable load. However, the conventional small prefilled syringe has a structure unsuitable for being kept pressed against the skin with a strong force, which is awkward to use.

US 2009/0105663 A discloses an example of a pharmaceutical liquid administration device with improved operability. US 2009/0105663 A discloses a technique to cover an outer periphery of a prefilled syringe with a syringe holder for covering a needle tube after administration, thereby enlarging a diameter of the entire device. In the technique disclosed in US 2009/0105663 A, a lock adapter provided to a distal end portion of the prefilled syringe is attached via a screw attachment with an administration component such as a needle hub having a needle tube.

SUMMARY

However, according to the technique described in US 2009/0105663 A, covering the syringe with the syringe holder enlarges the diameter of the entire device so that large rotational torque is generated when screwing the needle hub or the administration component. Therefore, the syringe moves in a radial direction, which may cause damage on a claw portion configured to restrict rotation of the syringe. Accordingly, the syringe rotates inside the syringe holder, and the syringe holder spins around, which is a problem.

The concepts described in this application have been made in view of such situations, and one object of certain embodiments is to provide a syringe holder and a pharmaceutical liquid administration set which can inhibit a syringe from spinning around inside the syringe holder when attaching an administration component.

According to one embodiment, a syringe holder is configured to hold a syringe that comprises a body section having a cylindrical shape capable of being filled with a pharmaceutical liquid therein; a discharge portion formed at a distal end portion of the body section; a flange that is formed at a proximal end portion of the body section and includes a first portion apart from a central axis of the body section by a predetermined distance and a second portion apart from the central axis by a distance shorter than the predetermined distance of the first portion; and a screw portion that is provided to the discharge portion and is configured to screw an administration component to administer the pharmaceutical liquid to a biological body. The syringe holder includes a barrel body, a holder opening, a fixing claw, a fixing projection, a deformation promoting portion, a rotation restricting portion, and a radial movement-restricting portion. The barrel body is formed in a cylindrical shape, covering at least an outer peripheral surface of the flange of the syringe. The holder opening is provided to the barrel body and the syringe is inserted. The fixing claw fixes a surface of the flange in a side close to the holder opening. The fixing projection fixes a surface of the flange in a side opposite to the surface in the side close to the holder opening. The deformation promoting portion is provided close to an end portion of the fixing claw in a side opposite to the holder opening, being configured to promote the fixing claw to deform outward in a radial direction of the barrel body when the first portion of the syringe inserted from the holder opening climbs over the fixing claw. Being brought into contact with the second portion, the rotation restricting portion restricts the syringe from rotating in a circumferential direction with respect to the barrel body. The radial movement-restricting portion is provided close to the deformation promoting portion. Being brought into contact with the first portion, the radial movement-restricting portion restricts the syringe from moving in the radial direction with respect to the barrel body.

In another embodiment, a pharmaceutical liquid administration set include the syringe and the syringe holder described above.

According to a syringe holder and a pharmaceutical liquid administration set described above, it is possible to inhibit the syringe holder from spinning around when attaching an administration component to a syringe.

DETAILED DESCRIPTION

Figure 1:
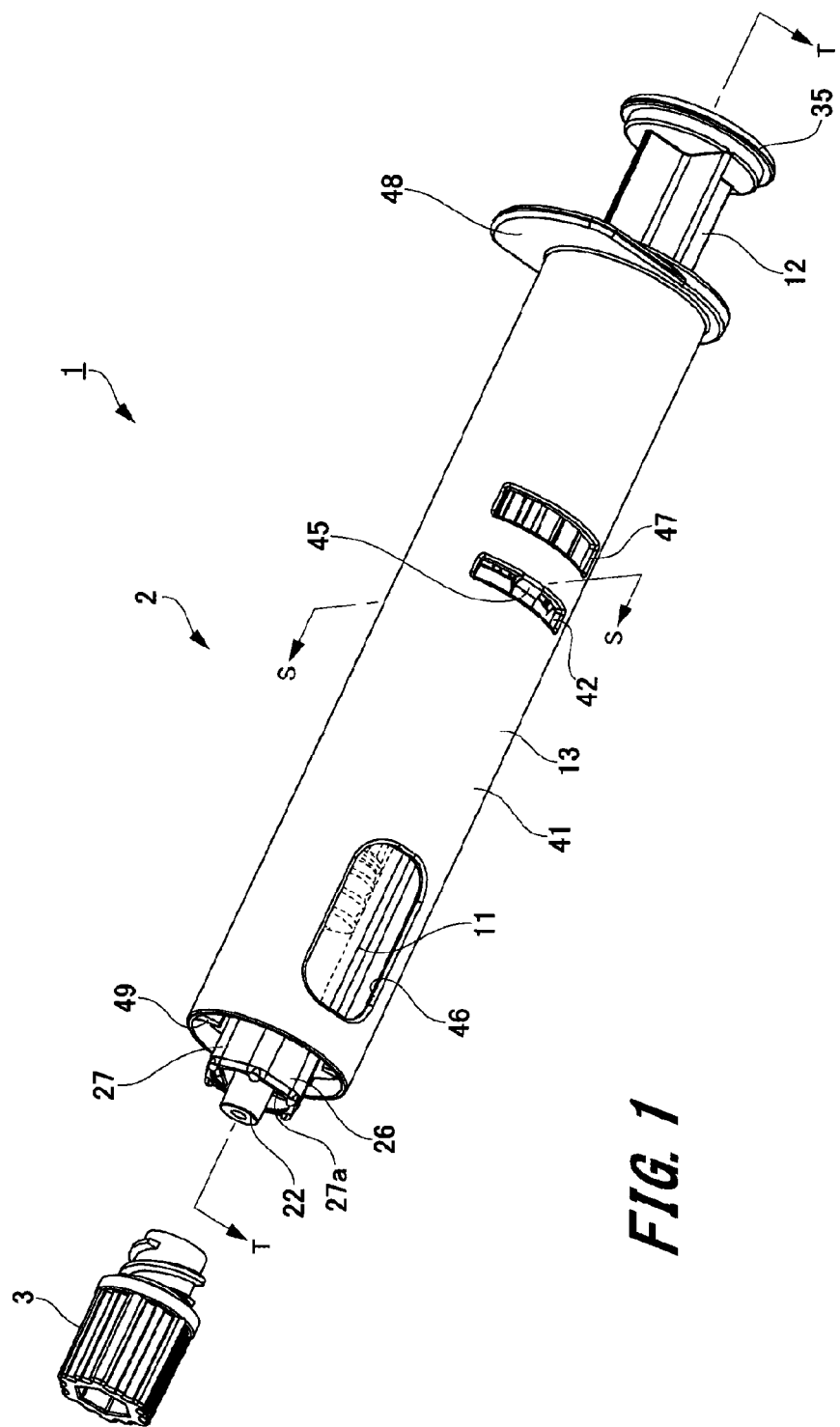
FIG. 1 is a perspective view illustrating a pharmaceutical liquid administration device including a syringe holder according to an embodiment of the present invention.

Hereinafter, an embodiment of a syringe holder and a pharmaceutical liquid administration set will be described with reference to FIGS. 1 to 17. In each of the drawings, the same members are denoted with the same reference numerals. It should be noted that the present invention is not limited to the following embodiment.

The description will be given in the following order.

1. Embodiment 1-1. Configuration of Pharmaceutical Liquid Administration Device 1-2. Assembling of Pharmaceutical Liquid Administration Device (Method for Manufacturing Pharmaceutical Liquid Administration Device)

1. Embodiment 1-1. Configuration of Pharmaceutical Liquid Administration Device

With reference to FIGS. 1 to 11, hereinafter described is a configuration of a pharmaceutical liquid administration device having a syringe holder according to an embodiment of the present invention.

Figure 2:
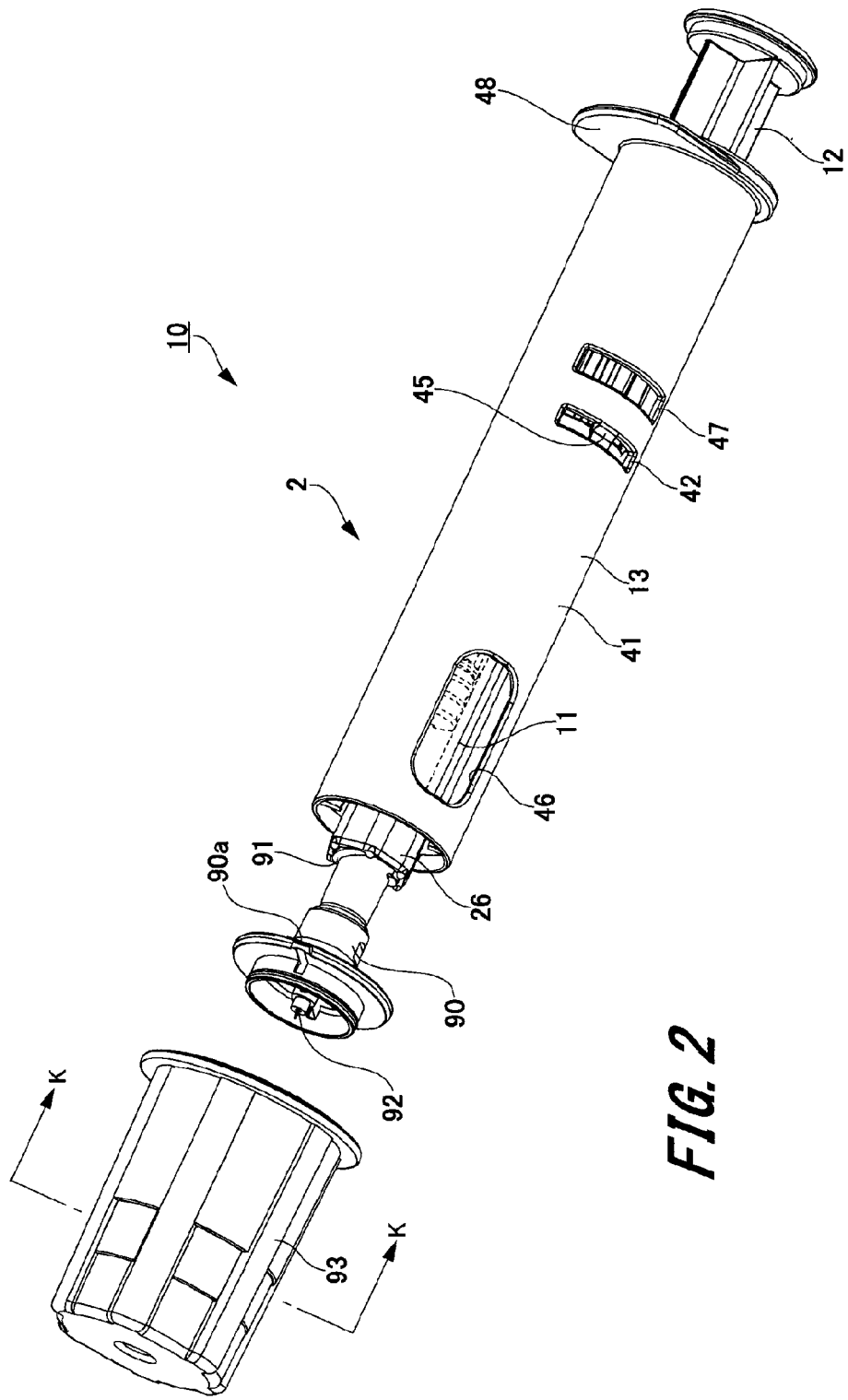
FIG. 2 is a perspective view illustrating a state where an administration component is mounted on the pharmaceutical liquid administration device according to one embodiment.
Figure 3:
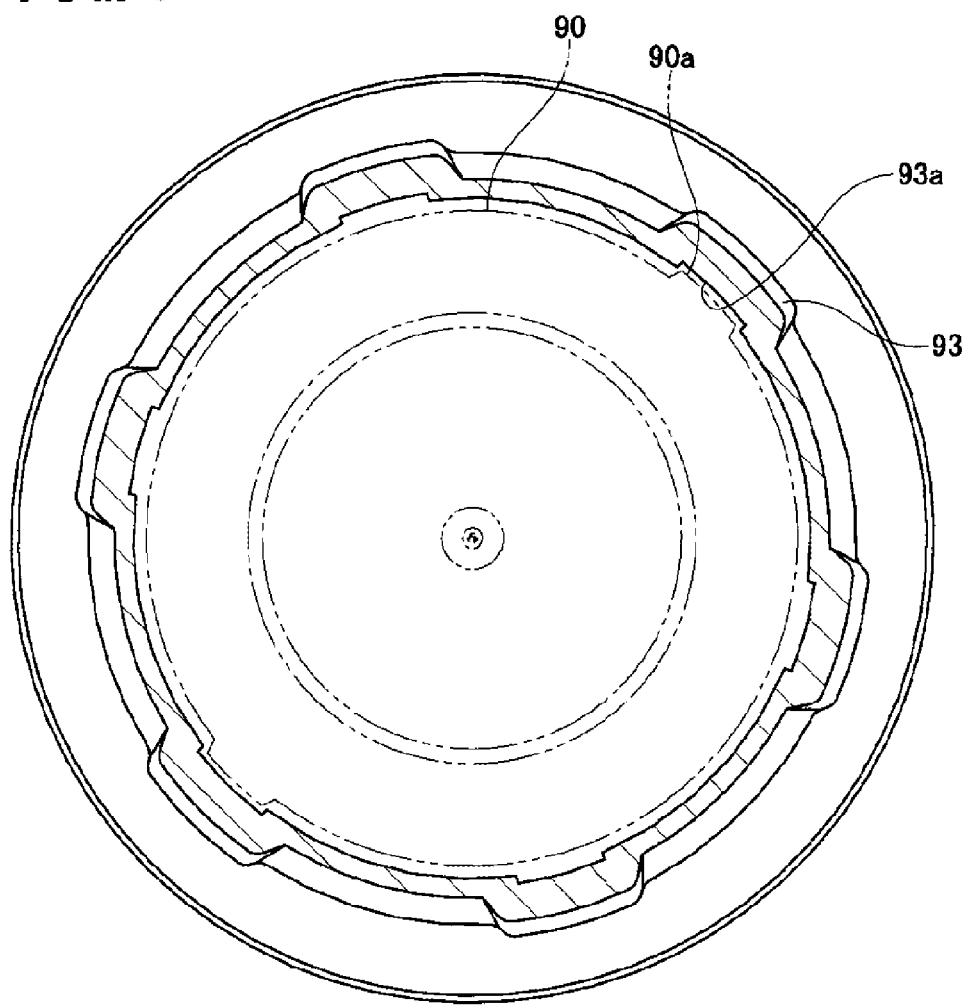
FIG. 3 is a cross-sectional view taken along the line K-K illustrated in FIG. 2.
Figure 4:
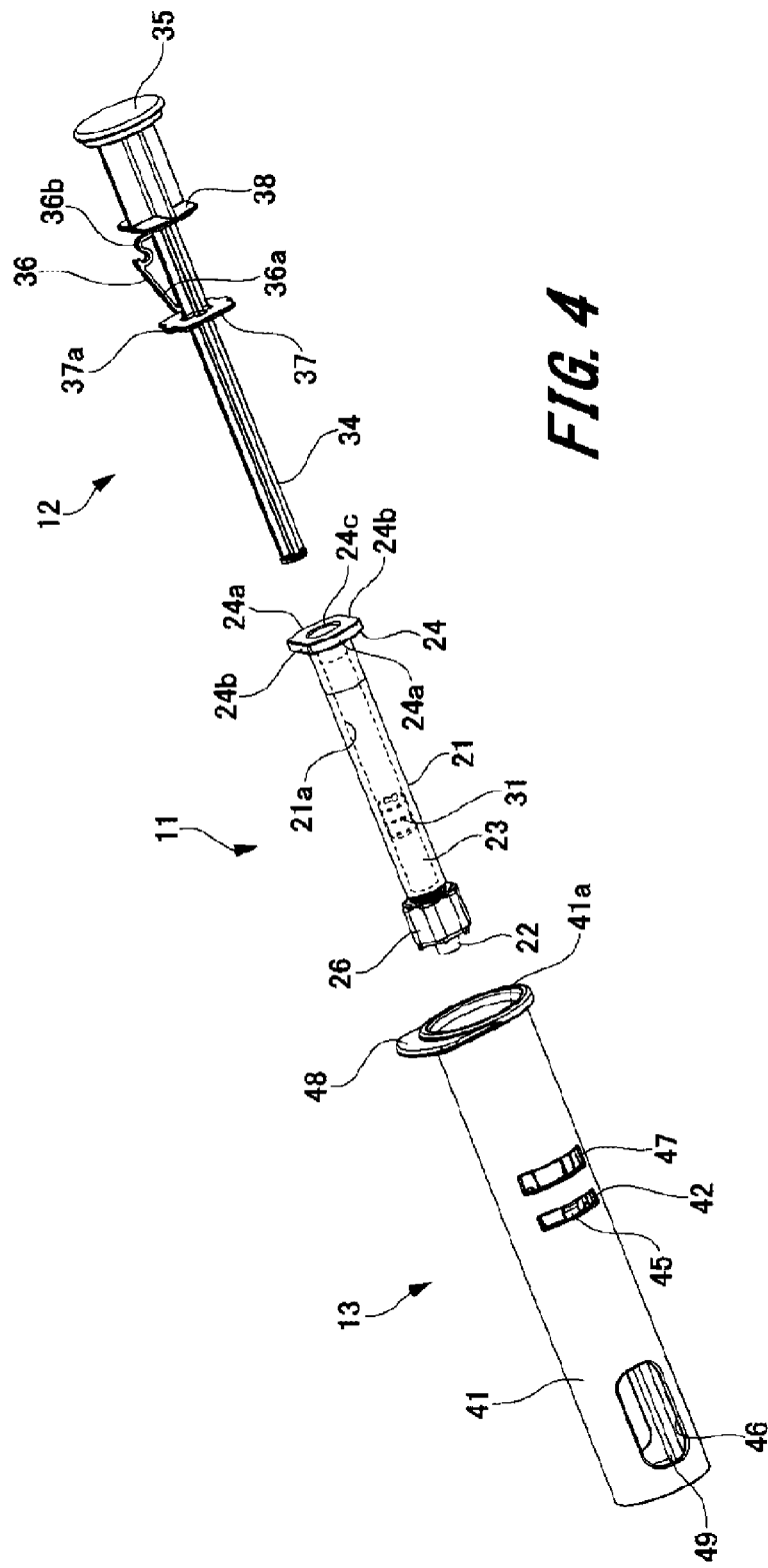
FIG. 4 is an exploded perspective view illustrating the pharmaceutical liquid administration device according to one embodiment.
Figure 5:
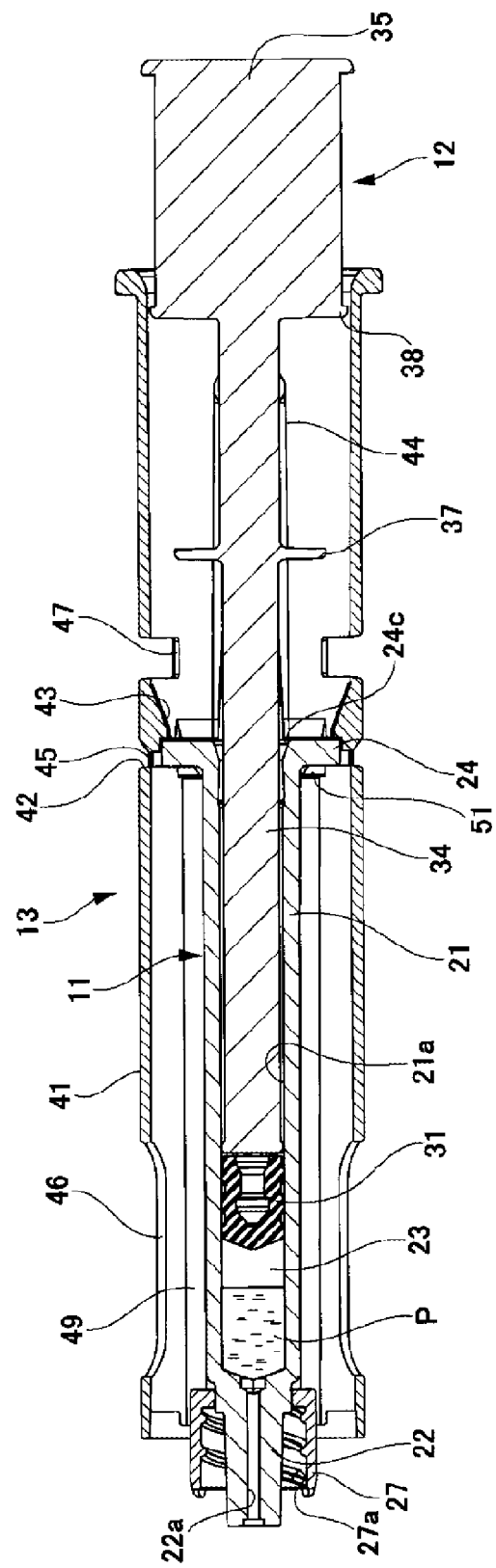
FIG. 5 is a cross-sectional view taken along the line T-T illustrated in FIG. 1.
Figure 6:
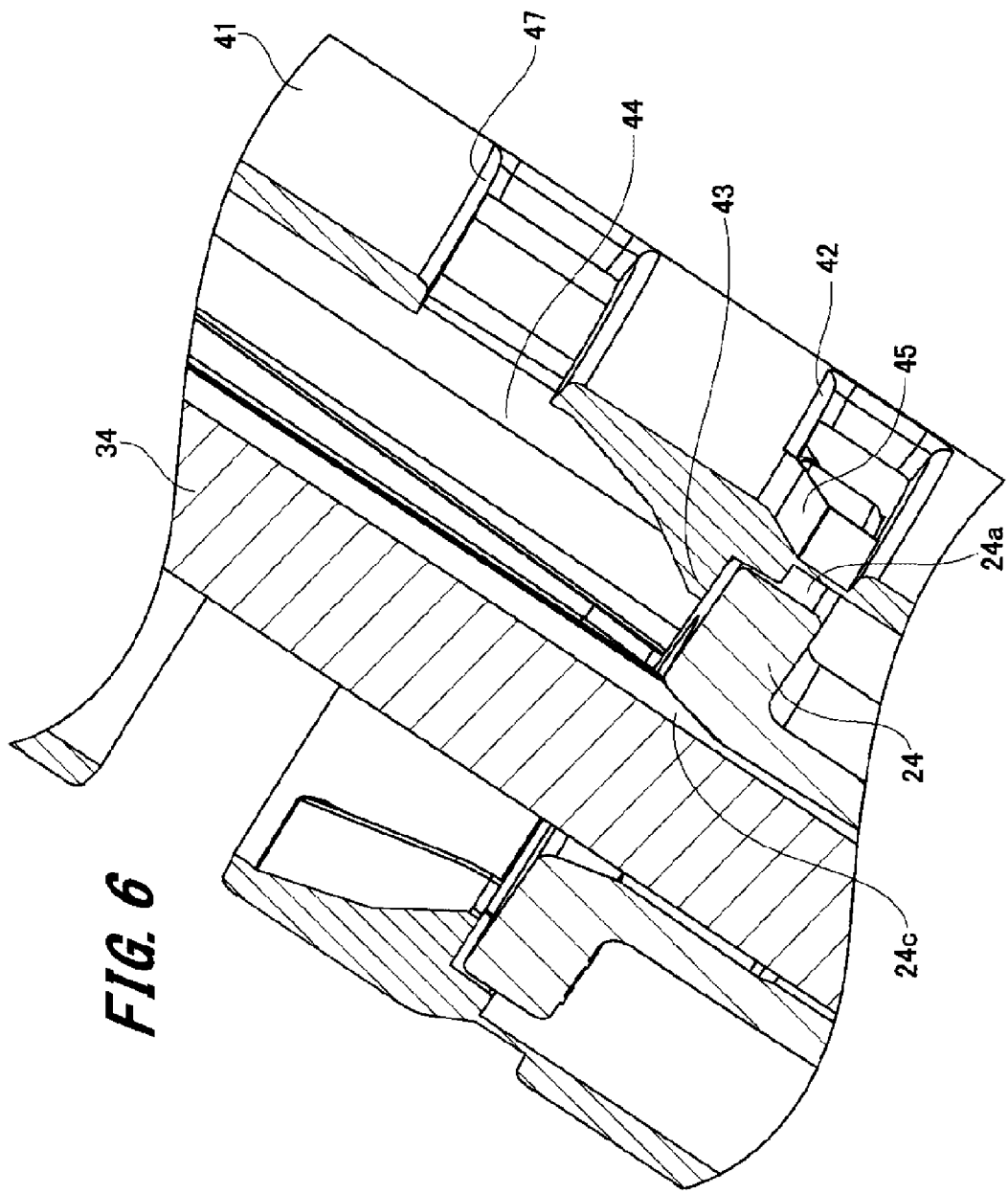
FIG. 6 is an enlarged cross-sectional view of main parts in FIG. 5.
Figure 7:
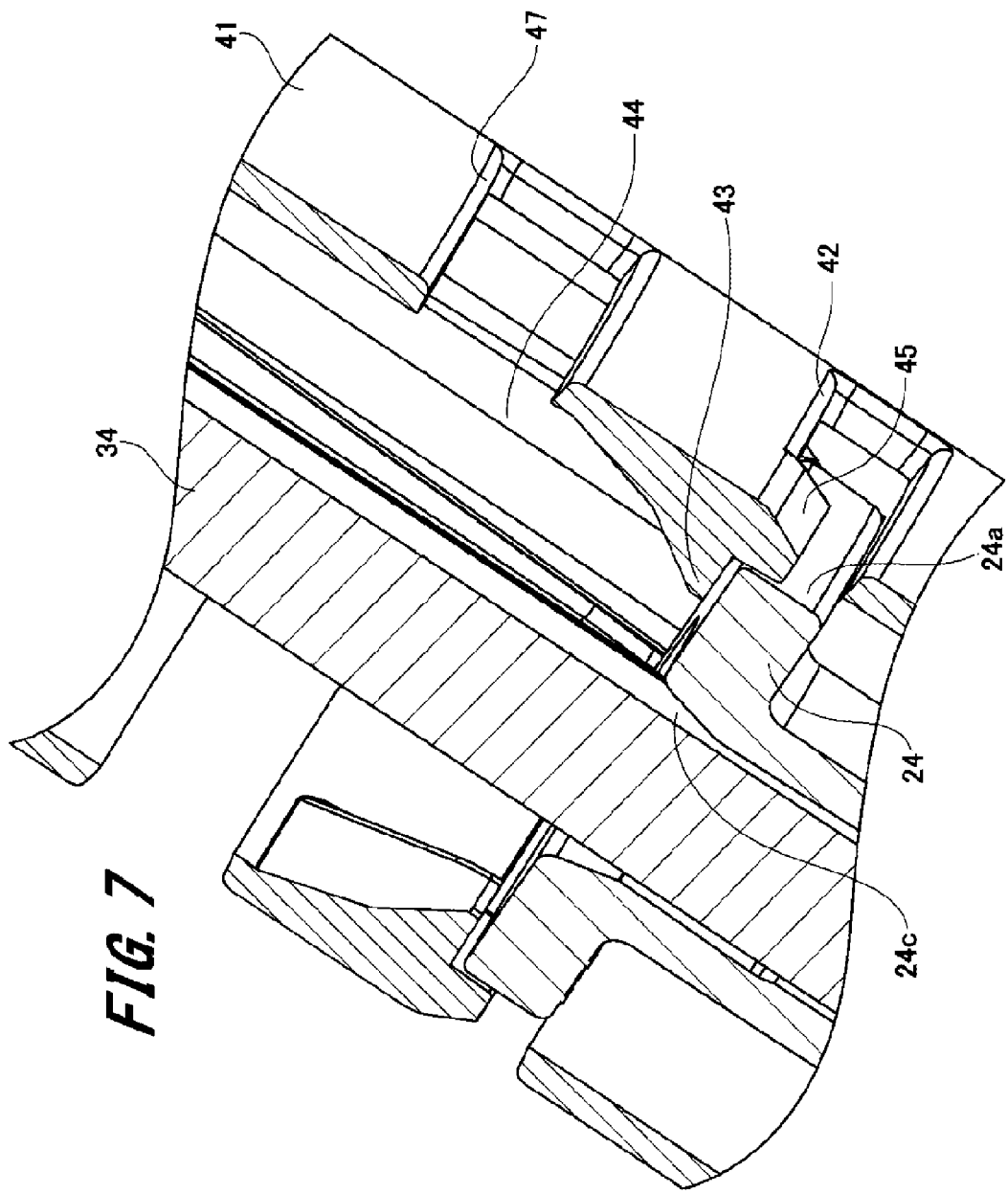
FIG. 7 is an enlarged cross-sectional view illustrating main parts of a syringe holder according to one embodiment.
Figure 8:
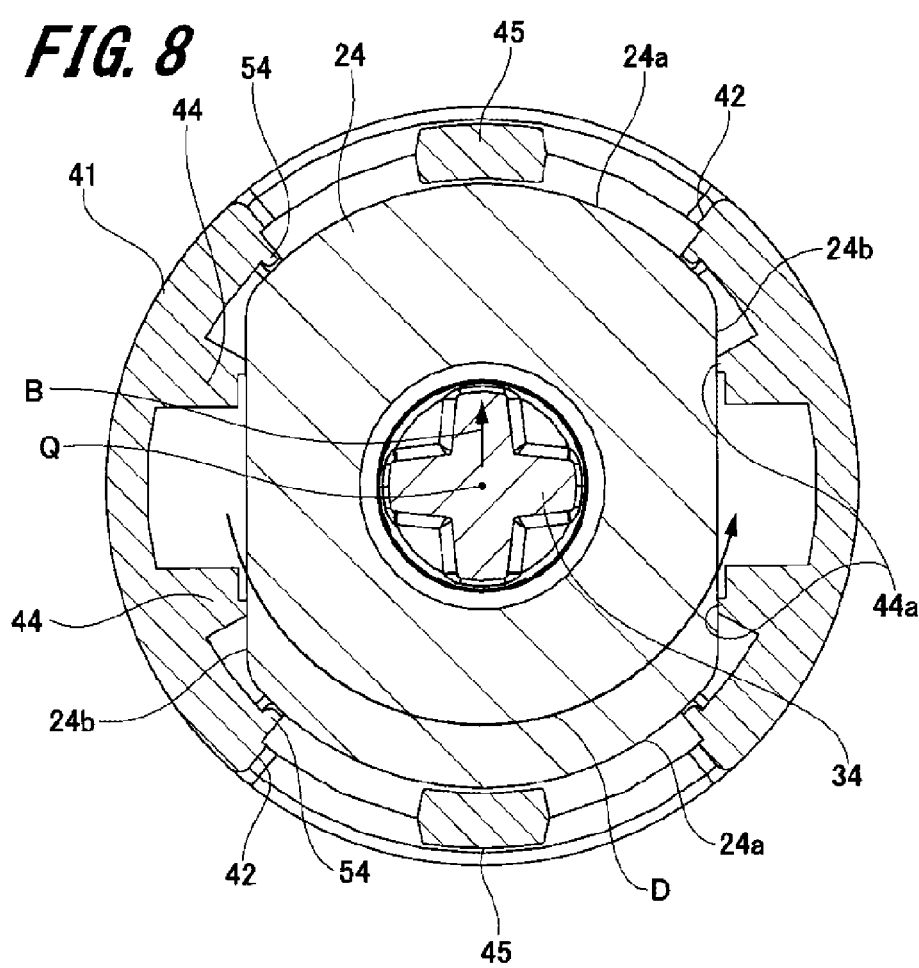
FIG. 8 is a cross-sectional view taken along the line S-S illustrated in FIG. 1.
Figure 9:
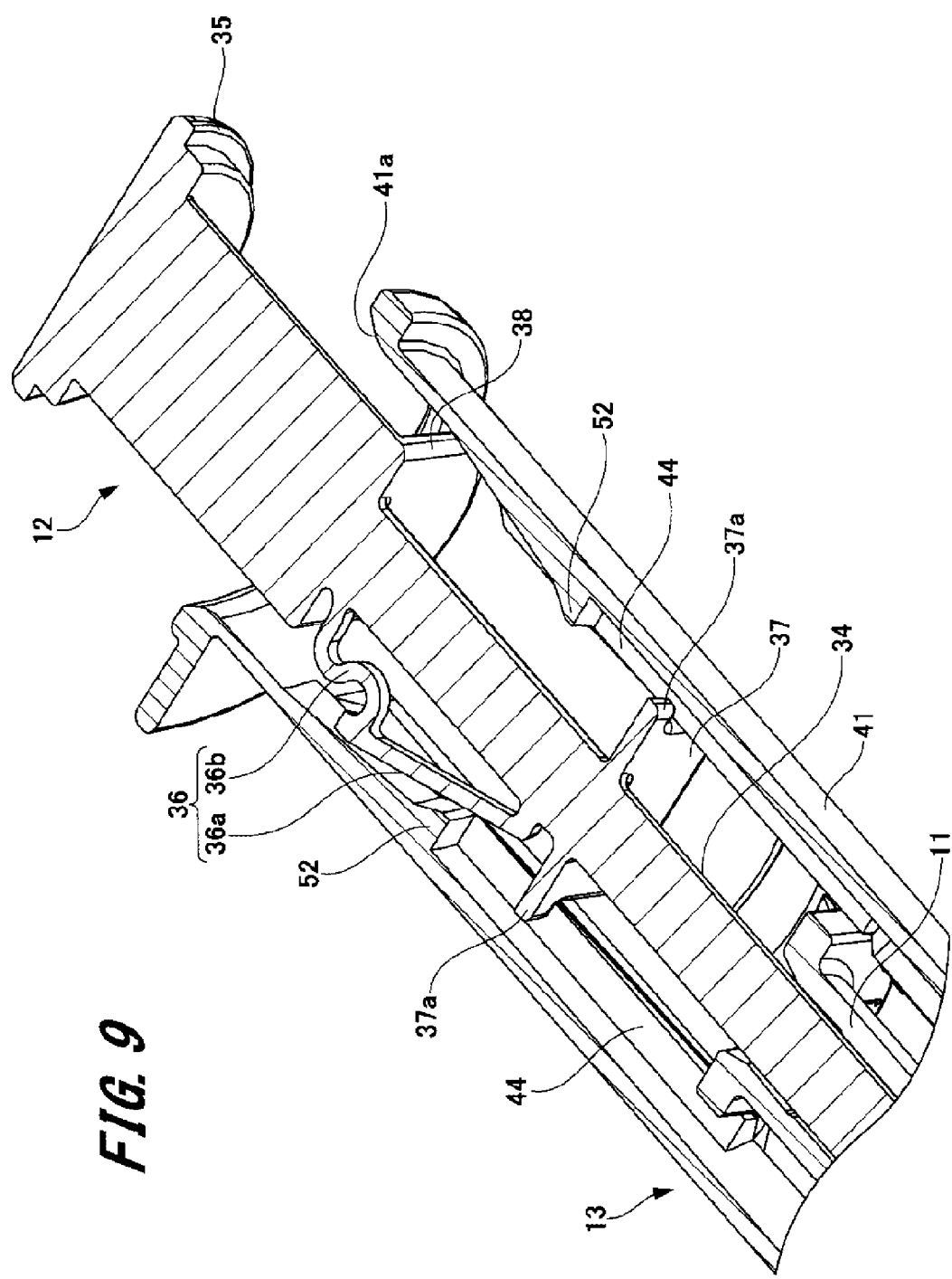
FIG. 9 is an enlarged cross-sectional view illustrating main portions of the syringe holder and a pusher member according to one embodiment.
Figure 10:
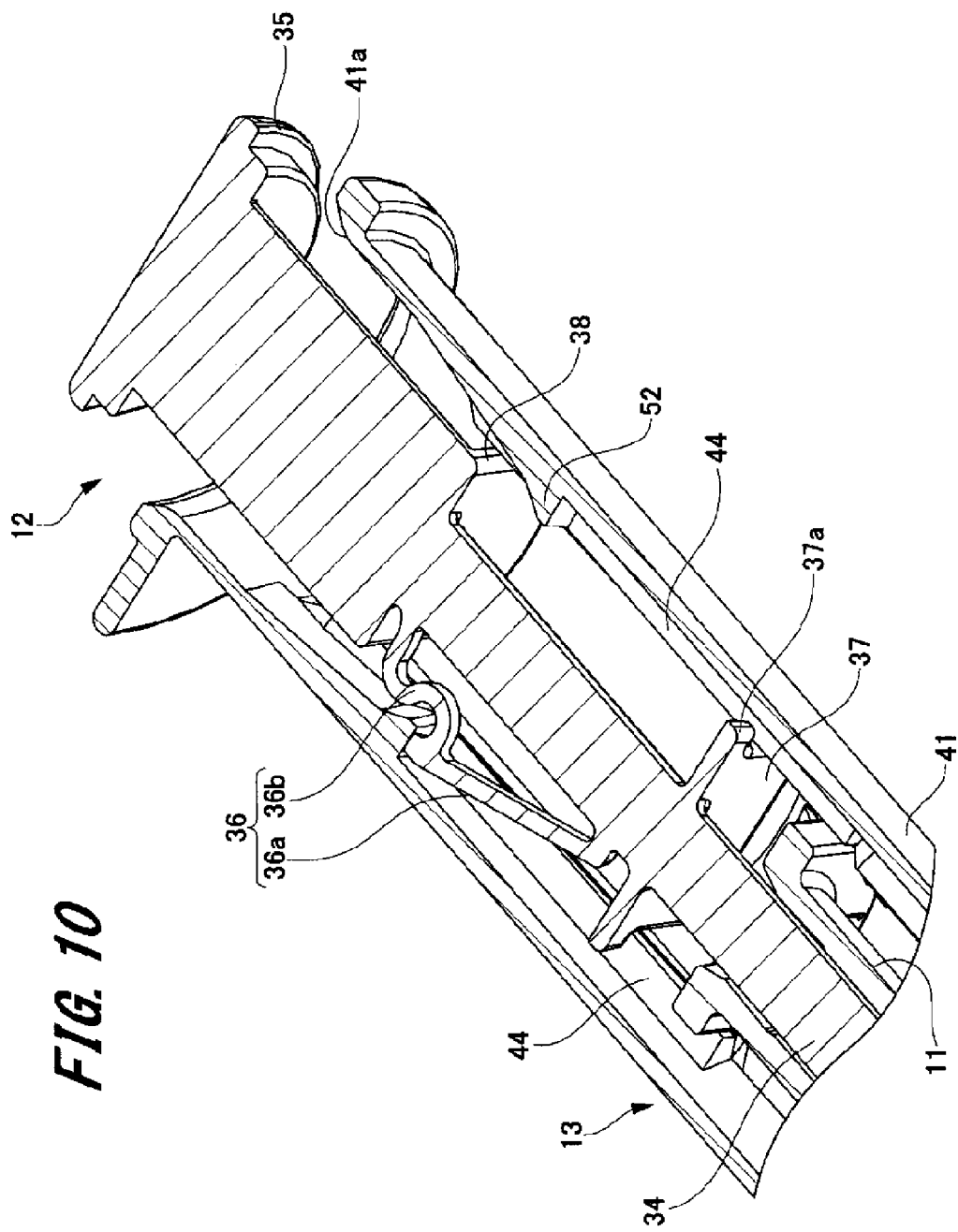
FIG. 10 is a cross-sectional view illustrating a state where the pusher member is slid from the state illustrated in FIG. 9.
Figure 11:
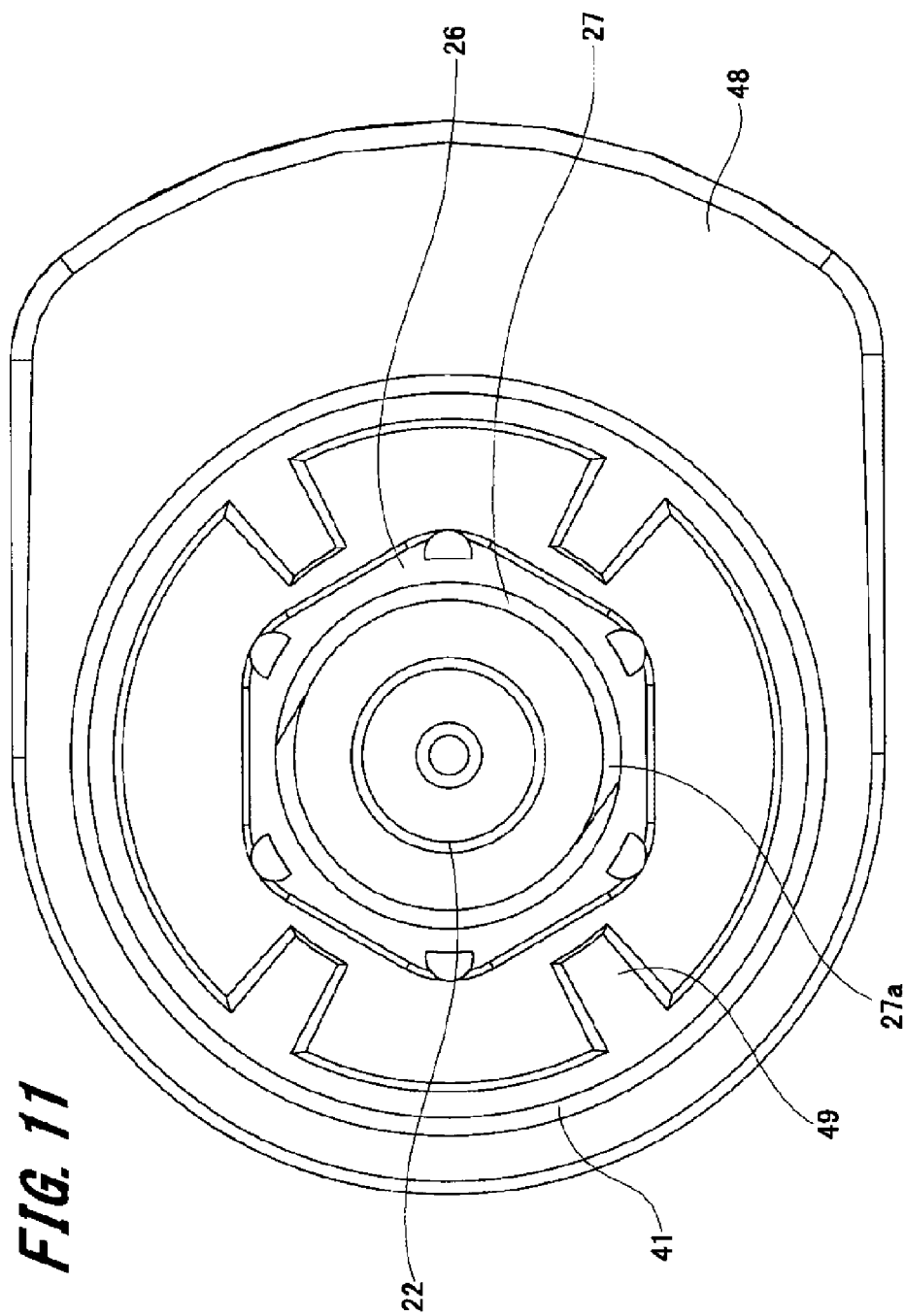
FIG. 11 is a front view illustrating the pharmaceutical liquid administration device according to one embodiment.

FIG. 1 is a perspective view illustrating the pharmaceutical liquid administration device according to this embodiment. FIG. 2 is a perspective view illustrating a state where an administration component is mounted on the pharmaceutical liquid administration device according to this embodiment. FIG. 3 is a cross-sectional view taken along the line K-K illustrated in FIG. 2. FIG. 4 is an exploded perspective view of the pharmaceutical liquid administration device according to this embodiment. FIG. 5 is a cross-sectional view taken along the line T-T illustrated in FIG. 1; and FIG. 6 is an enlarged cross-sectional view of main parts in FIG. 5. FIG. 7 is an enlarged cross-sectional view illustrating a modification of the main parts in FIG. 6. FIG. 8 is a cross-sectional view taken along the line S-S illustrated in FIG. 1. FIGS. 9, 10 are cross-sectional views illustrating main parts of a pusher member and the syringe holder in the pharmaceutical liquid administration device according to this embodiment. FIG. 11 is a front view illustrating the pharmaceutical liquid administration device according to this embodiment.

As illustrated in FIG. 1, a pharmaceutical liquid administration device 1 includes an administration device body 2; and a cap 3 detachably attached to the administration device body 2. As illustrated in FIG. 2, this pharmaceutical liquid administration device 1 is mounted with an injection needle assembly 90 by screwing the same into a distal end portion of the administration device body 2. The injection needle assembly 90 is an example of an administration component, having a needle tube 92. The administration device body 2 and the injection needle assembly 90 are included in a pharmaceutical liquid administration set 10.

The skin is composed of three parts: epidermis, dermis, and subcutaneous tissue. The epidermis is a layer having a thickness of about 50 to 200 μm from a skin surface; and the dermis is a layer having a thickness of about 1.5 to 3.5 mm, continuous from the epidermis. An influenza vaccine is typically administered subcutaneously or intramuscularly so that the vaccine is administered to a lower part of the skin or deeper.

There have been studies on administering an influenza vaccine to an upper part of the skin including many immunocompetent cells as a target site so as to reduce an injected quantity of the vaccine. Note that the upper part of the skin refers to epidermis and dermis of the skin. The pharmaceutical liquid administration device 1 according to this embodiment is used for intradermal injection with respect to the upper part of the skin as a target site.

The injection needle assembly 90 is provided with a male threaded portion 91 (an example of a screw portion), and an engaging portion 90a. Furthermore, the injection needle assembly 90 is housed in a storage case 93.

The storage case 93 is formed in a hollow cylindrical shape with a proximal end portion opened and a distal end portion closed. As illustrated in FIG. 3, a cylindrical hole in the storage case 93 includes an engaged portion 93a which is to be engaged with the engaging portion 90a of the injection needle assembly 90. Accordingly, the injection needle assembly 90 rotates together with the storage case 93 when the injection needle assembly 90 is mounted on the administration device body 2 of the pharmaceutical liquid administration device 1 by screwing. In regard to the storage case 93, an outer diameter of a cylindrical portion that houses the injection needle assembly 90 is set, for example, within a range of 10 to 30 mm.

As illustrated in FIG. 4, the administration device body 2 includes a syringe 11; a pusher member 12; and a syringe holder 13 that holds the syringe 11.

[Syringe]

The syringe 11 is a prefilled syringe filled with a pharmaceutical liquid P in advance. The syringe 11 includes a body section 21 formed in a substantially cylindrical shape; a discharge portion 22 formed at a distal end portion of the body section 21; and a gasket 31.

The gasket 31 is slidably disposed in a cylindrical hole 21*a* of the body section 21. The gasket 31 is formed in a substantially columnar shape. The gasket 31 moves while being in contact with an inner peripheral surface of the cylindrical hole 21*a* of the body section 21 in a liquid-tight manner. As illustrated in FIG. 5, the gasket 31 partitions a space in the cylindrical hole 21*a* of the body section 21 into two. A space inside the discharge portion 22 as well as a space inside the body section 21 from the gasket 31 to the discharge portion 22 are included in a liquid chamber 23 filled with the pharmaceutical liquid P. On the other hand, a space inside the body section 21 from the gasket 31 to the other end is where a pusher body 34 (to be mentioned) of the pusher member 12 is to be disposed.

One end portion of the gasket 31 is formed into a tapered shape having a diameter continuously decreasing toward a distal end. This tapered shape corresponds to a shape of an inner surface in the distal end portion of the body section 21. Therefore, when the gasket 31 is moved to a side closer to the distal end portion of the body section 21, one end portion of the gasket 31 comes into contact with the inner surface in the distal end portion of the body section 21 so as not to generate a gap.

A material of the gasket 31 is not specifically limited, but an elastic material is preferable in order to improve liquid tightness with respect to the body section 21. Examples of the elastic material include various rubber materials such as natural rubber, isobutylene rubber, and silicone rubber, various thermoplastic elastomers such as thermoplastic olefin and thermoplastic styrene, and mixtures thereof.

In regard to the body section 21, an inner diameter and an outer diameter are appropriately set in accordance with use application or a volume of the pharmaceutical liquid filled in the liquid chamber 23. For example, in a case where the volume is set to 0.5 mL, the inner diameter of the body section 21 is preferably set within a range of 4.4 to 5.0 mm, and the outer diameter within a range of 6.6 to 8.4 mm. In a case where the volume is set to 1 mL, the inner diameter of the body section 21 is preferably set within a range of 6.1 to 9.0 mm, and the outer diameter within a range of 7.9 to 12.5 mm.

Examples of the pharmaceutical liquid P include various vaccines for inhibiting various infectious diseases such as influenza, but the pharmaceutical liquid P is not limited to vaccines. Other than vaccines, examples of the pharmaceutical liquid P include injection solutions of glucide such as glucose, injection solutions for correcting electrolytes such as sodium chloride and potassium lactate, vitamins, antibiotic injection solutions, contrast media, steroids, proteolytic enzyme inhibitors, fat emulsions, anticancer agents, anesthetics, heparin calcium, and antibody drugs.

Furthermore, the body section 21 is provided with a flange 24 in its proximal end portion. The flange 24 protrudes outward in a radial direction from an outer peripheral surface of the proximal end portion of the body section 21. The flange 24 has first portions 24*a* extending a first distance from a central axis of the body section 21; and second portions 24*b* extending a second distance from the central axis, the second distance being smaller than the first distance.

A pair of the first portions 24*a* and a pair of the second portions 24*b* face each other across the central axis. The two first portions 24*a* are respectively fixed with two fixing claws 43 (to be mentioned) of a barrel body 41 included in the syringe holder 13.

The maximum outer diameter of the flange 24, that is, a distance between the pair of first portions 24*a* is set, for example, within a range of 10 to 20 mm. In this embodiment, the first portions 24*a* are formed in an arc shape with the central axis of the body section 21 serving as the center, and the second portions 24*b* are formed in a linear shape in a planar view from the proximal end portion.

The flange 24 is formed with an opening 24*c* communicating with the cylindrical hole 21*a* of the body section 21. The opening 24*c* opens in a circular shape, and the pusher body 34 (to be mentioned) of the pusher member 12 is inserted into the opening 24*c*.

The discharge portion 22 is continuously disposed in one end of the body section 21, being formed in a substantially cylindrical shape coaxial with the body section 21. The discharge portion 22 is formed in a tapered shape in which a diameter continuously decreases toward the distal end opposite to the body section 21. The discharge portion 22 includes a cylindrical hole 22*a* communicating with the cylindrical hole 21*a* of the body section 21.

The discharge portion 22 is coupled with a Luer Lock portion 26, an example of a screw portion. The Luer Lock portion 26 includes a cylindrical portion 27 having a cylindrical shape, coaxially surrounding the discharge portion 22. The cylindrical portion 27 has a circular inner periphery and a hexagonal outer periphery. As illustrated in FIG. 5, the inner peripheral surface of the cylindrical portion 27 is formed with a female threaded portion 27*a*. The female threaded portion 27*a* is formed to be screwed with the male threaded portion 91 provided to the injection needle assembly 90. As the Luer Lock portion 26 is screwed with the injection needle assembly 90, the injection needle assembly 90 is attached to a distal end portion of the syringe 11. Accordingly, a needle hole of the needle tube 92 in the injection needle assembly 90 and the inside of the discharge portion 22 are communicated with each other in a liquid-tight manner.

Examples of a material of the syringe 11 include various resin such as polyvinyl chloride, polyethylene, polypropylene, cyclic polyolefin, polystyrene, poly-(4-methylpentene-1), polycarbonate, acrylic resin, acrylonitrile-butadiene-styrene copolymer, polyester such as polyethylene terephthalate, and also include butadiene-styrene copolymer, and polyamide (for example, nylon-6, nylon-6, 6, nylon-6, 10, and nylon-12). Among these examples, it is preferable to use resin such as polypropylene, cyclic polyolefin, polyester, poly-(4-methylpentene-1) from a viewpoint of moldability. It is preferable that the material of the syringe 11 is substantially transparent in order to ensure the visibility of the inside.

[Pusher Member]

The pusher member 12 includes a pusher body 34 to press the gasket 31; an operating portion 35; a lock portion 36; a first collar 37; and a second collar 38. The pusher body 34 is formed in a substantially rod-like shape whose cross-sectional shape in a direction orthogonal to an axial direction of the pusher body 34 is substantially formed in a cross shape. The pusher body 34 is inserted into the body section 21 from the opening 24*c* of the syringe 11, being mostly disposed inside the body section 21 of the syringe 11.

A distal end face of the pusher body 34 is formed in a substantially circular shape. As the operating portion 35 (to be mentioned) is pushed in the distal end direction, the distal end face of the pusher body 34 comes into contact with the gasket 31 disposed inside the body section 21 of the syringe 11, which causes the gasket 31 to slide in the distal end direction.

Figure 13:
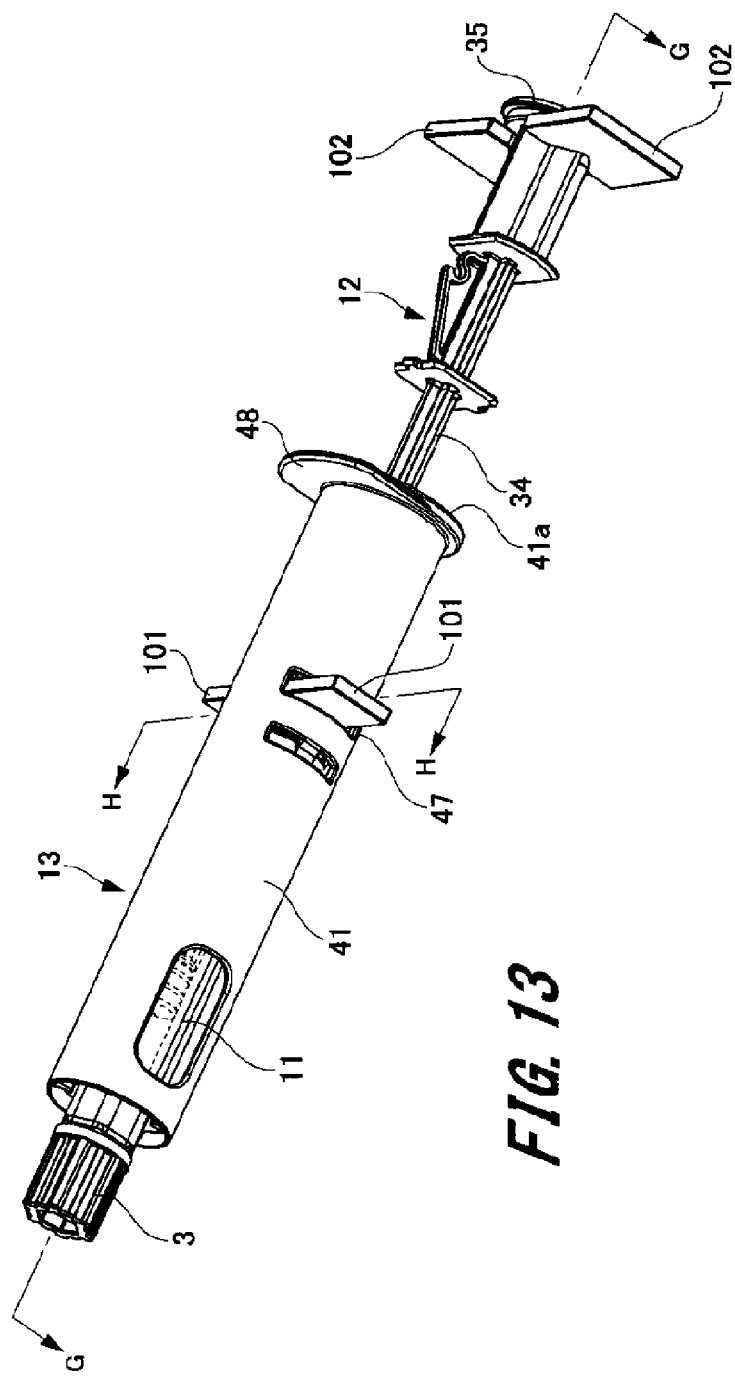
FIG. 13 is a perspective view illustrating a state right before the pusher member being mounted on the pharmaceutical liquid administration device according to one embodiment.

The pusher body 34 has an outer diameter d1 set within a range of 0.01 to 3 mm smaller than the inner diameter of the body section 21 (see FIG. 13). Specifically, in a case where the volume of the pharmaceutical liquid filled in the liquid chamber 23 is 0.5 mL, the outer diameter d1 of the pusher body 34 is preferably set within a range of 1.5 to 4.9 mm, and in a case where the volume of the pharmaceutical liquid filled in the liquid chamber 23 is 1.0 mL, the outer diameter d1 is preferably set within a range of 3.2 to 8.8 mm.

Figure 14:
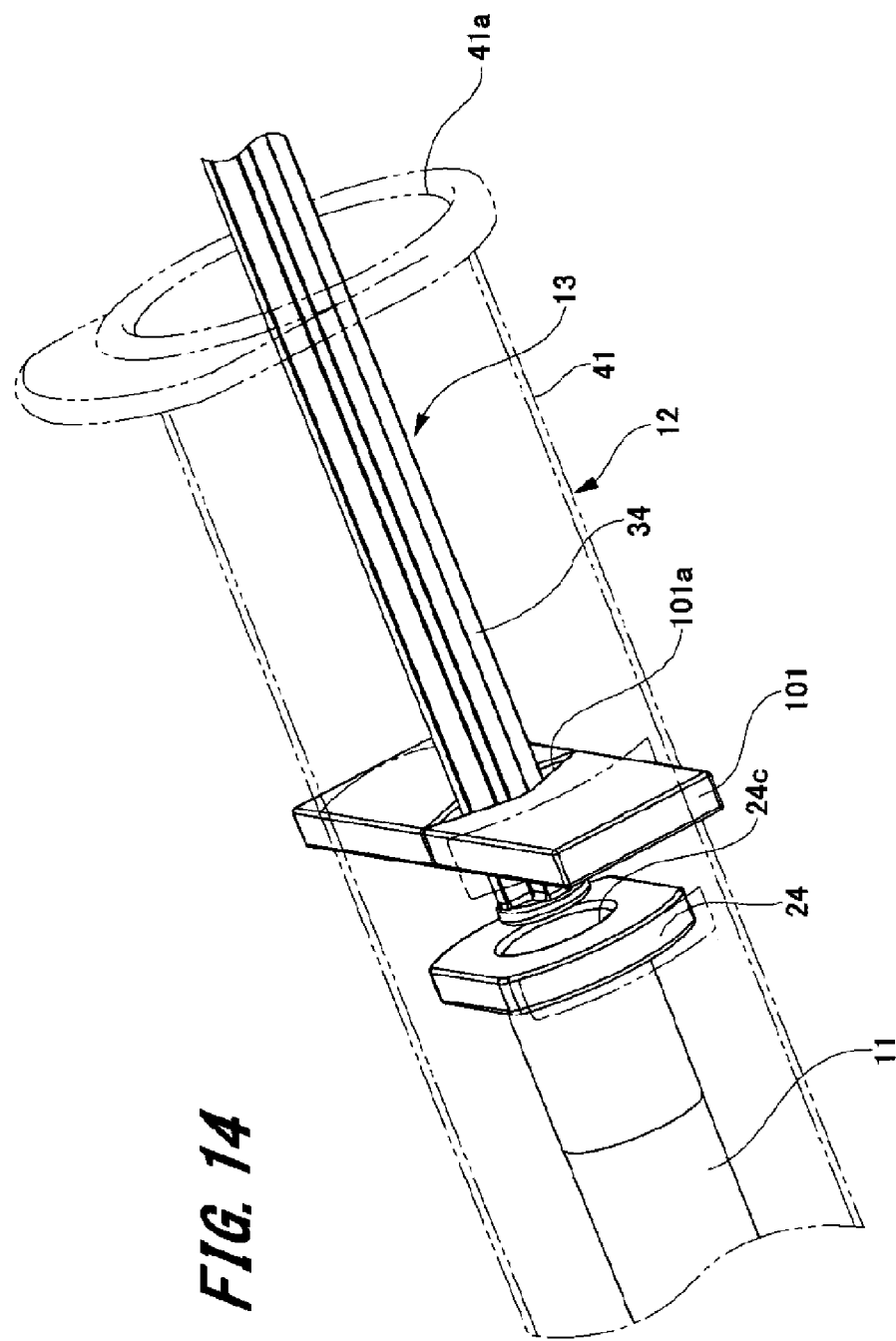
FIG. 14 is an enlarged perspective view illustrating main parts in a state where the pusher member is mounted on the pharmaceutical liquid administration device according to one embodiment.

The pusher body 34 has a length L4, an axial length from the distal end of the pusher body 34 to the first collar 37 (to be mentioned), which is substantially equivalent to an axial length of the body section 21 of the syringe 11 (see FIG. 14). Specifically, the axial length L4 of the pusher body 34 is preferably set within a range of 30 to 60 mm. Furthermore, the length L4 of the pusher body 34 is preferably set within a range of 8 to 25 times the size of the outer diameter d1.

The operating portion 35, lock portion 36, first collar 37, and second collar 38 are disposed in a proximal end portion of the pusher body 34 in the following order, that is, the first collar 37, lock portion 36, second collar 38, and operating portion 35.

The first collar 37 and second collar 38 are formed in a rectangular flat plate shape. The first collar 37 and second collar 38 protrude from side surfaces of the pusher body 34 in a direction orthogonal to the axial direction of the pusher body 34. The first collar 37 is provided with an anti-drop projection 37a at an edge portion. The anti-drop projection 37a protrudes from the edge portion of the first collar 37, being disposed in parallel to a plane of the first collar 37. When the pusher body 34 is inserted into the cylindrical hole 21a of the body section 21, the anti-drop projection 37a comes into contact with a protuberant portion 52 (to be mentioned) of the syringe holder 13. Accordingly, it is possible to inhibit the pusher member 12 from falling off the syringe 11 and the syringe holder 13. The lock portion 36 is provided between the first collar 37 and second collar 38.

The lock portion 36 protrudes from a side surface of the pusher body 34 in a direction orthogonal to the axial direction of the pusher body 34. The lock portion 36 includes an inclined portion 36a, and an elastic portion 36b. The inclined portion 36a is inclined inward in the distal end direction, being disposed in a distal end portion of the lock portion 36. The elastic portion 36b has elasticity, being disposed in a proximal end portion of the lock portion 36. When pushing the gasket 31 to the end, the lock portion 36 is fixed with the protuberant portion 52 (to be mentioned) of the syringe holder 13 (see FIG. 11).

The operating portion 35 is formed at the proximal end of the pusher body 34. The operating portion 35 is formed in a substantially disk-like shape. When using the pharmaceutical liquid administration device 1, a user presses the operating portion 35 so that the gasket 31 disposed in the distal end of the pusher body 34 moves inside the cylindrical hole 21a of the body section 21 of the syringe 11. As a material of this pusher member 12, polyacetal as well as various resins enumerated as the material of the syringe 11 can be employed.

[Syringe Holder]

The syringe holder 13 includes the barrel body 41; through holes 42 illustrated as an example of deformation promoting portions; the fixing claws 43; rotation restricting portions 44; radial movement-restricting portions 45; a viewing window 46; insertion holes 47; and a holder collar 48.

The barrel body 41 is formed in a substantially cylindrical shape, being configured to cover the outer peripheral surface of the body section 21 and the flange 24 of the syringe 11 and the outer peripheral surface of the cylindrical portion 27 of the Luer Lock portion 26. The barrel body 41 is configured to be graspable by the user when the injection needle assembly 90 is mounted on the syringe 11. A proximal end portion of the barrel body 41 is formed with a holder opening 41a into which the syringe 11 and the pusher member 12 can be inserted.

The holder opening 41a is placed closer to the distal end than the operating portion 35 which is the proximal end portion of the pusher body 34 inserted into the syringe holder 13. Note that the barrel body 41 may cover at least the outer peripheral surface of the flange 24.

In regard to the barrel body 41, an inner diameter is set larger than the outer diameters of the body section 21, cylindrical portion 27, and flange 24, which is, for example, within a range of 11 to 21 mm. Furthermore, an outer diameter of the barrel body 41 is set, for example, within a range of 15 to 25 mm.

The viewing window 46 is opened in a distal end portion of the barrel body 41. The viewing window 46 is provided to a position where the liquid chamber 23 of the syringe 11 can be viewed from the outside of the syringe holder 13 when the syringe 11 is mounted on the syringe holder 13. Accordingly, even when the syringe holder 13 is mounted on the syringe 11, it is possible to ensure visibility of the inside.

Furthermore, the holder collar 48 is provided to the proximal end portion of the barrel body 41. The holder collar 48 protrudes substantially perpendicularly from a part of an outer peripheral surface of the barrel body 41. Due to the holder collar 48, when the user grips the syringe holder 13 and administers the pharmaceutical liquid, it is possible to inhibit the finger holding the syringe holder 13 from slipping toward the proximal end. It is also possible to inhibit the pharmaceutical liquid administration device 1 from rolling over when placing the pharmaceutical liquid administration device 1 on a desk and the like.

Furthermore, when the syringe 11 and the pusher member 12 are inserted into the barrel body 41 from the holder opening 41a, it is possible to determine an orientation in which the syringe 11 and the pusher member 12 are inserted in accordance with a second portion of the holder collar 48.

As illustrated in FIGS. 5 and 6, the two fixing claws 43 are provided protruding from an inner wall of the barrel body 41 in a middle part in an axial direction of the inner wall of the barrel body 41. The two fixing claws 43 are provided at positions in the inner wall of the barrel body 41 where they face each other. As illustrated in FIG. 6, distal end faces of the fixing claws 43 face a proximal end face of the flange 24 continuing to the first portions 24a.

As illustrated in FIG. 5, fixing projections 51 are provided to a side closer to the distal end than the two fixing claws 43. When the syringe 11 is inserted into the syringe holder 13, the flange 24 climbs over the fixing claws 43 and is fitted between the fixing claws 43 and the fixing projections 51. Accordingly, the syringe 11 is restricted to move axially with respect to the syringe holder 13.

In this embodiment, the number of the fixing claws 43 is described to be two as an example, but the present invention is not limited thereto, and the number of the fixing claws 43 may be three or more.

Furthermore, through holes 42 are respectively provided close to the two fixing claws 43. The through holes 42 are formed at a side closer to the distal end than the fixing claws 43. In other words, the through holes 42 are provided at positions farther from the holder opening 41a than the fixing claws 43.

As illustrated in FIG. 8, the through holes 42 are opened, having a predetermined length along a circumferential direction of the barrel body 41. When the syringe 11 is inserted into the barrel body 41, the first portions 24a of the flange 24 face the through holes 42. Since the through holes 42 are provided close to the fixing claws 43, when the first portions 24a of the flange 24 climb over the fixing claws 43, the fixing claws 43 are easily deformed outward in a radial direction of the barrel body 41. Accordingly, it possible to inhibit damage on the flange 24 and the fixing claws 43 when the first portions 24a of the flange 24 climb over the fixing claws 43.

Furthermore, the two through holes 42 has a length in the circumferential direction of the barrel body 41 set within a range of 9 to 25 mm. In other words, the circumferential length of each of the two through holes 42 is set to 15 to 35% of an outer peripheral length of the barrel body 41. Accordingly, it is possible to maintain strength of the barrel body 41 while promoting the outward deformation of the fixing claws 43 in the radial direction of the barrel body 41.

In this embodiment, the deformation promoting portions are described as the through holes 42 penetrating side walls of the barrel body 41, but the present invention is not limited thereto. The deformation promoting portions may have any shape as long as the fixing claws 43 are easily deformed outward in the radial direction of the barrel body 41 when the first portions 24a of the flange 24 climb over the fixing claws 43. Therefore, the first portions 24a may be thin-thickness portions formed by reducing the inner wall of the barrel body 41, that is specifically, recessed portions provided to the inner wall of the barrel body 41.

Each of the two through holes 42 is provided with the radial movement-restricting portion 45. As illustrated in FIG. 8, the radial movement-restricting portions 45 are provided in the middle of the through holes 42 in the circumferential direction. As illustrated in FIG. 6, the radial movement-restricting portions 45 extend from distal ends of the fixing claws 43 in the distal end direction so as to close a part of the through holes 42, serving as projections that connect distal ends of the through holes 42 and proximal ends thereof. As illustrated in FIG. 8, the radial movement-restricting portions 45 are brought into contact with or disposed close to the first portions 24a of the flange 24.

Herein, due to torque generated when the injection needle assembly 90 is screwed into the pharmaceutical liquid administration device 1 (see FIG. 2), a force represented by the arrow B illustrated in FIG. 8, or a force in a direction in which a central axis Q of the syringe 11 is decentered, is applied to the syringe 11. In other words, a force is applied to the syringe 11 in the radial direction. Therefore, the syringe 11 may move in the radial direction, and the flange 24 may thrust into the through holes 42. In this embodiment, in order to solve such a problem, the radial movement-restricting portions 45 are brought into contact with the first portions 24a of the flange 24 so that the syringe 11 is restricted to move in the radial direction.

As illustrated in FIG. 6, distal end portions of the radial movement-restricting portions 45 are formed thinner than proximal end portions which are to be brought into contact with the first portions 24a of the flange 24. Accordingly, it becomes difficult to restrict the fixing claws 43 to deform outward in the radial direction of the barrel body 41, and it is possible to reliably restrict the syringe 11 to move in the radial direction when the first portions 24a of the flange 24 climb over the fixing claws 43.

In this embodiment, the radial movement-restricting portions 45 are described as parts that connect distal end portions and proximal end portions of the through holes 42, but the present invention is not limited thereto. The radial movement-restricting portions 45 may not be configured to connect the distal end portions and the proximal end portions of the through holes 42. Specifically, as illustrated in FIG. 7, the radial movement-restricting portions 45 may extend in the distal end direction from the distal ends of the fixing claws 43 part way in an axial direction of the through holes 42 so as to close a part of the through holes 42. In other words, the radial movement-restricting portions 45 may have a shape with thin distal end portions omitted. In such a case, since the radial movement-restricting portions have free distal ends, it is possible to easily deform the fixing claws 43 outward in the radial direction of the barrel body 41, and to reliably inhibit damage on the flange 24 and the fixing claws 43 when the first portions 24a of the flange 24 climb over the fixing claws 43.

As illustrated in FIGS. 4 and 5, the two insertion holes 47 are formed, penetrating the side walls of the barrel body 41 in a side close to the holder opening 41a of the opening 24c of the syringe 11 which is held inside the barrel body 41. The two insertion holes 47 are arranged to face each other. The insertion holes 47 are formed at a side closer to the proximal end of the barrel body 41 than the fixing claws 43 and the through holes 42. When the pusher member 12 is inserted into the syringe 11, guide members 101 (see FIG. 13) that guide the pusher body 34 are inserted into the insertion holes 47.

Each length L1 (see FIG. 15) in a direction orthogonal to an axial direction of the two insertion holes 47 is set larger than the outer diameter d1 of the pusher body 34. It is preferable that the length L1 is substantially equivalent to a distance between the two second portions 24b of the flange 24, which are facing each other.

In this embodiment, the number of the insertion holes 47 provided to the barrel body 41 is described to be two as an example, but the present invention is not limited thereto. Three or more insertion holes 47 into which the guide members 101 are inserted may be provided to the barrel body 41. In a case where three or more insertion holes 47 are provided, it is preferable to arrange the insertion holes 47 at equal intervals in the circumferential direction of the barrel body 41 in order to guide the pusher body 34 in a well-balanced manner.

Furthermore, as illustrated in FIGS. 5 and 8, the rotation restricting portions 44 are provided between the two through holes 42 in the inner wall of the barrel body 41. The rotation restricting portions 44 are four ribs protruding from an inner wall surface of the barrel body 41. The rotation restricting portions 44 are brought into contact with or disposed close to the second portions 24b of the flange 24. The rotation restricting portions 44 are brought into contact with the second portions 24b of the flange 24 inserted into the barrel body 41 so as to restrict the rotation of the syringe 11 in the circumferential direction with respect to the syringe holder 13.

As illustrated in FIGS. 5, 9, and 10, the rotation restricting portions 44 extend from the vicinity of the through holes 42, having a predetermined length toward the holder opening 41a of the barrel body 41. Accordingly, when the syringe 11 is inserted from the holder opening 41a, the rotation restricting portions 44 are brought into contact with the second portions 24b of the flange 24 so as to restrict the rotation of the syringe 11 in the circumferential direction with respect to the syringe holder 13.

As illustrated in FIG. 8, an inner end portion of each of the rotation restricting portions 44 is provided with a contact projection 44a which is to be brought into contact with each of the second portions 24b of the flange 24. Accordingly, it is possible to restrict the syringe 11 more reliably to rotate in the circumferential direction with respect to the syringe holder 13. As the contact projections 44a and the flange 24 are brought into contact with each other, it is also possible to inhibit the syringe 11 from rattling inside the barrel body 41.

Furthermore, as illustrated in FIG. 9, the first collar 37 of the pusher member 12 is brought into contact with the rotation restricting portions 44. Accordingly, it is possible to inhibit the pusher member 12 from rattling inside the barrel body 41.

Still further, the inner wall of the barrel body 41 is provided with protuberant portion 52 in a side closer to the proximal end portion. The protuberant portion 52 is provided between two adjacent rotation restricting portions 44 of the four rotation restricting portions 44. The protuberant portion 52 is a protrusion projecting inward in the radial direction from the inner wall of the barrel body 41. A distal end portion of the protuberant portion 52 projects substantially perpendicularly from the inner wall of the barrel body 41, while a proximal end portion thereof is inclined with respect to the inner wall of the barrel body 41.

When the pusher body 34 of the pusher member 12 is inserted into the barrel body 41 from the holder opening 41a, the anti-drop projection 37a climbs over the protuberant portion 52 and moves in a direction closer to the distal end portion than the protuberant portion 52. The anti-drop projection 37a can be brought into contact with the protuberant portion 52 from a side closer to the distal end, that is, from a side opposite to the holder opening 41a. Accordingly, it is possible to inhibit the pusher member 12 from falling off the barrel body 41.

When the pusher member 12 is operated to discharge the pharmaceutical liquid filled in the syringe 11, the lock portion 36 of the pusher member 12 climbs over the protuberant portion 52 of the syringe holder 13 as illustrated in FIG. 10. When the lock portion 36 climbs over the protuberant portion 52, the inclined portion 36a of the lock portion 36 is pressed against the protuberant portion 52, and the elastic portion 36b is elastically deformed. When the lock portion 36 has completely climbed over the protuberant portion 52, the elastic deformation of the elastic portion 36b returns to its original state. At this time, the operating portion 35 transmits a clicking sensation or a clicking sound to the user. Accordingly, it is possible to inform the user that the injection and administration of the pharmaceutical liquid have been completed.

Furthermore, when the lock portion 36 climbs over the protuberant portion 52, the lock portion 36 is fixed to the protuberant portion 52. Therefore, the pusher member 12 is restricted to move in a direction closer to the proximal end, that is, in a direction close to the holder opening 41a. Accordingly, it is possible to inhibit the used pharmaceutical liquid administration device 1 from being reused by mistake. Furthermore, the first collar 37 and the second collar 38 of the pusher member 12 are brought into contact with the rotation restricting portions 44. Accordingly, when the pusher member 12 is operated, it is possible to inhibit the pusher member 12 from rattling inside the cylindrical hole of the barrel body 41.

As illustrated in FIG. 8, rib members 54 are provided between the rotation restricting portions 44 and the through holes 42. A plurality of rib members 54 is provided to the inner wall surface of the barrel body 41, protruding from the inner wall surface of the barrel body 41. The plurality of rib members 54 is brought into contact with the flange 24 of the syringe 11. Accordingly, it is possible to inhibit the syringe 11 from rattling inside the cylindrical hole of the barrel body 41.

Furthermore, as illustrated in FIGS. 5 and 11, a distal end portion in the inner wall of the barrel body 41 is provided with a plurality of inclination restricting ribs 49. The plurality of inclination restricting ribs 49 protrude from the inner wall surface of the barrel body 41, extending from the vicinity of the through holes 42 and the rotation restricting portions 44 to the distal end portion of the barrel body 41. As illustrated in FIG. 11, the plurality of inclination restricting ribs 49 are arranged so as to surround an outer periphery of the discharge portion 22 of the syringe 11 inserted into the barrel body 41 and the outer periphery of the cylindrical portion 27 of the Luer Lock portion 26. The plurality of inclination restricting ribs 49 are brought into contact with the Luer Lock portion 26 so as to restrict the inclination of the syringe 11. Accordingly, it possible to inhibit the syringe 11 from being inclined inside the cylindrical hole of the barrel body 41 when the pharmaceutical liquid is administered or when the injection needle assembly 90 is attached.

[Another Technical Problem]

As a conventional technique, WO 2013/046855 A describes a technique to cover an outer periphery of an inner structural body corresponding to a syringe, using a gripping member so as to increase a diameter of the entire device. In this conventional technique, there is provided a pusher to move a gasket that slides inside the inner structural body.

However, in the conventional technique, an opening in the inner structural body into which the pusher is inserted is disposed in the middle of the gripping member in an axial direction. Therefore, the opening in the inner structural body into which the pusher is inserted is apart from an opening in the gripping member into which the pusher is inserted. Thus, according to the technique disclosed in WO 2013/046855 A, when the pusher is inserted into the inner structural body, a shaft center of the pusher is likely to deviate from the center of the opening of the inner structural body, which makes it difficult to insert the pusher into the inner structural body.

Therefore, the present example also intends to provide a method for manufacturing a syringe holder, a pharmaceutical liquid administration set, and a pharmaceutical liquid administration device in which a distal end of a pusher body can be inserted into an opening of a syringe without deviation.

1-2. Assembling of Pharmaceutical Liquid Administration Device

Hereinafter, assembling of the pharmaceutical liquid administration device 1 (a method of manufacturing the pharmaceutical liquid administration device) will be described with reference to FIG. 4 and FIGS. 12 to 17.

FIGS. 12 to 17 are views for describing insertion of the pusher member 12.

To assemble the pharmaceutical liquid administration device 1, first, the Luer Lock portion 26 is coupled to the discharge portion 22 of the syringe 11 as illustrated in FIG. 4. Next, a male threaded portion of the cap 3 is screwed into the female threaded portion 27a of the Luer Lock portion 26, and the cap 3 is mounted on the Luer Lock portion 26. Accordingly, a discharge port of the discharge portion 22 in the syringe 11 is sealed with a packing provided to the cap 3.

Subsequently, the pharmaceutical liquid P is filled inside the body section 21 of the syringe 11. Then, the gasket 31 is inserted into the body section 21 from the opening 24c of the syringe 11.

Next, the syringe 11 is supported by a syringe support member (not illustrated), and the syringe 11 is inserted into the cylindrical hole of the barrel body 41 from the holder opening 41a of the barrel body 41 of the syringe holder 13. At this time, linear portions of the holder collar 48 of the barrel body 41 are oriented to the linear second portions 24b provided to the flange 24 of the syringe 11. Accordingly, it is possible to easily adjust an orientation in the circumferential direction of the syringe 11 with respect to the barrel body 41.

Since the length L1 of the insertion holes 47 is substantially equal to the distance between the two opposed second portions 24b of the flange 24, when the syringe 11 is inserted into the cylindrical hole of the barrel body 41, the flange 24 of the syringe 11 hardly enters the insertion holes 47, and the syringe 11 can be easily inserted to a specified position.

As illustrated in FIG. 5, the flange 24 of the syringe 11 is fitted between the fixing claws 43 of the barrel body 41 and the fixing projections 51, and a distal end face and a proximal end face of the flange 24 are fixed by the fixing projections 51 and the fixing claws 43, respectively. At this time, the fixing claws 43 can be easily elastically deformed by the through holes 42 provided close to end portions of the fixing claws 43 which are opposite to the holder opening 41a. As illustrated in FIGS. 6 and 8, the radial movement-restricting portions 45 face the first portions 24a, and the rotation restricting portions 44 face the second portions 24b.

Figure 12:
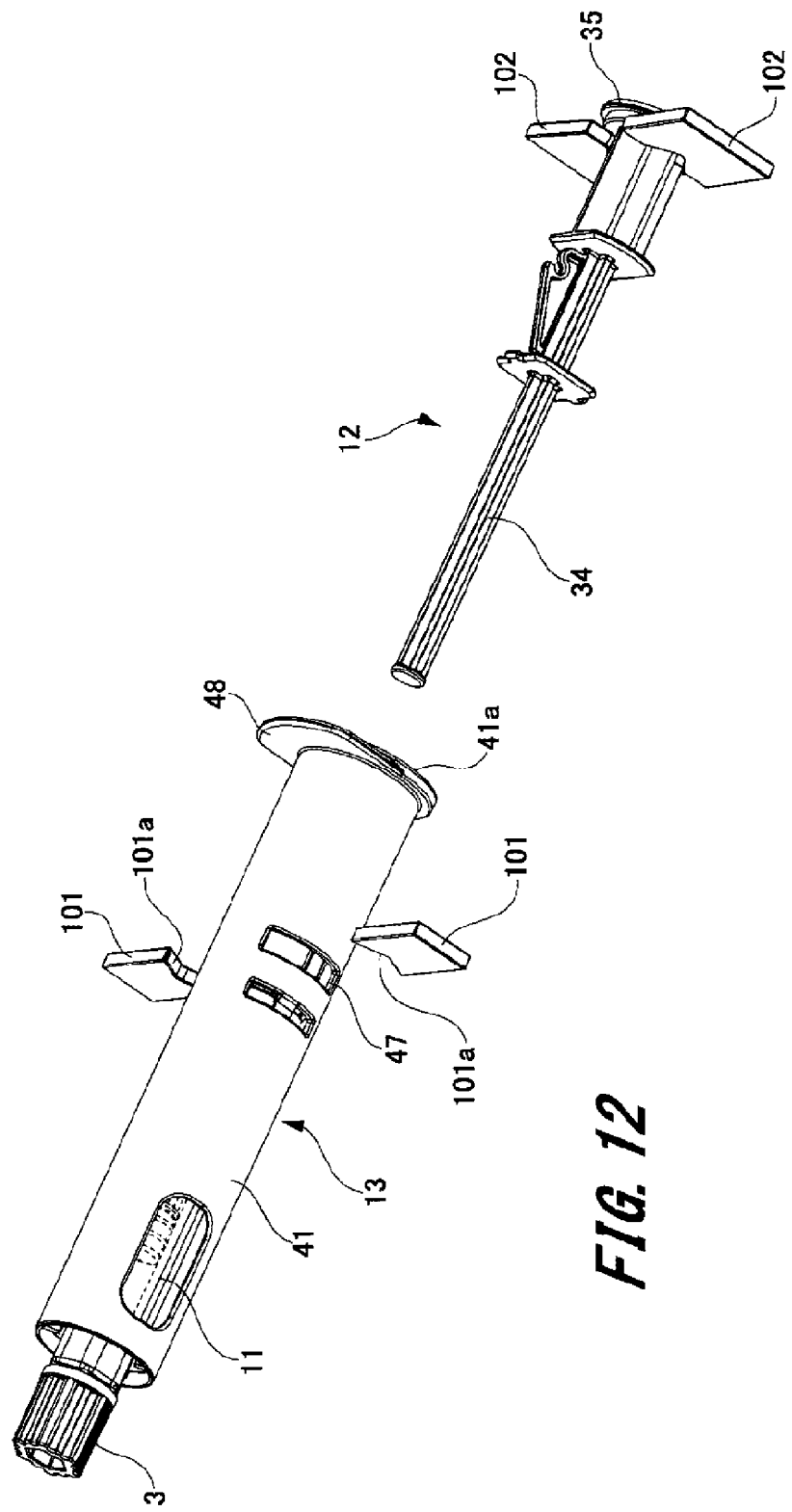
FIG. 12 is a perspective view for describing a state where the pusher member is to be mounted on the pharmaceutical liquid administration device according to one embodiment.

Next, as illustrated in FIG. 12, the syringe holder 13 holding the syringe 11 is supported by a syringe holder support member (not illustrated), and the pusher member 12 is supported by a chuck member 102. A pair of guide members 101 is caused to face the insertion holes 47 provided to the syringe holder 13.

Figure 15:
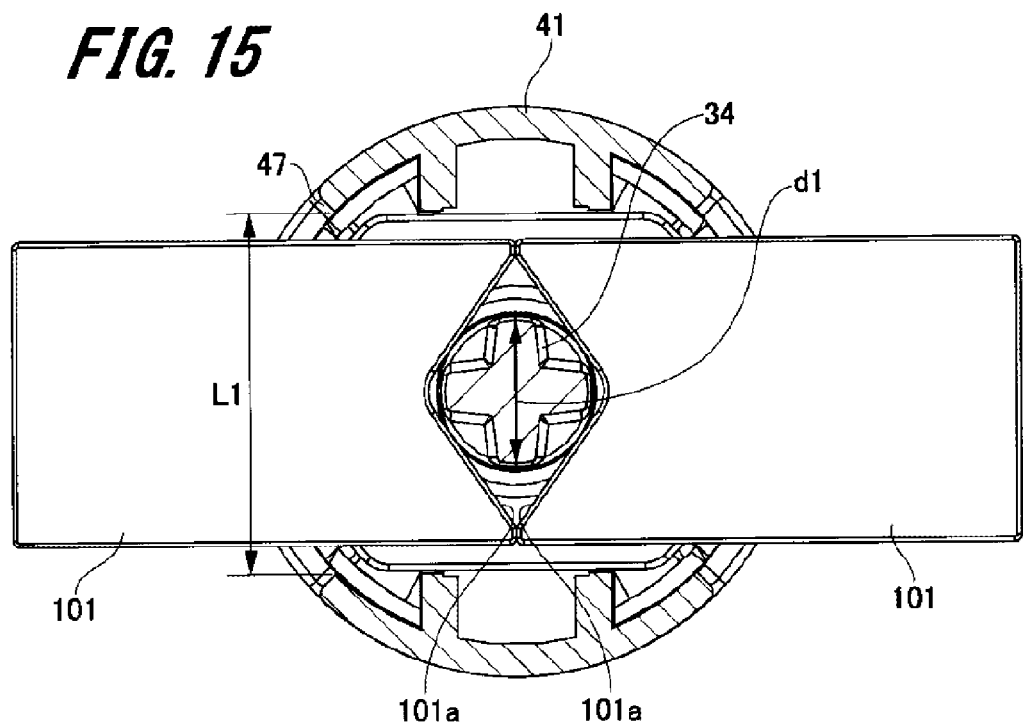
FIG. 15 is a cross-sectional view taken along the line H-H illustrated in FIG. 13.

Next, as illustrated in FIG. 13, the pusher member 12 supported by the chuck member 102 is inserted into the barrel body 41 from the holder opening 41a of the barrel body 41. The pair of guide members 101 is inserted into the barrel body 41 from the insertion holes 47. As illustrated in FIGS. 14 and 15, end portions of the guide members 101 facing side surfaces of the pusher member 12 are provided with guide grooves 101a substantially having a V-shape.

Figure 16:
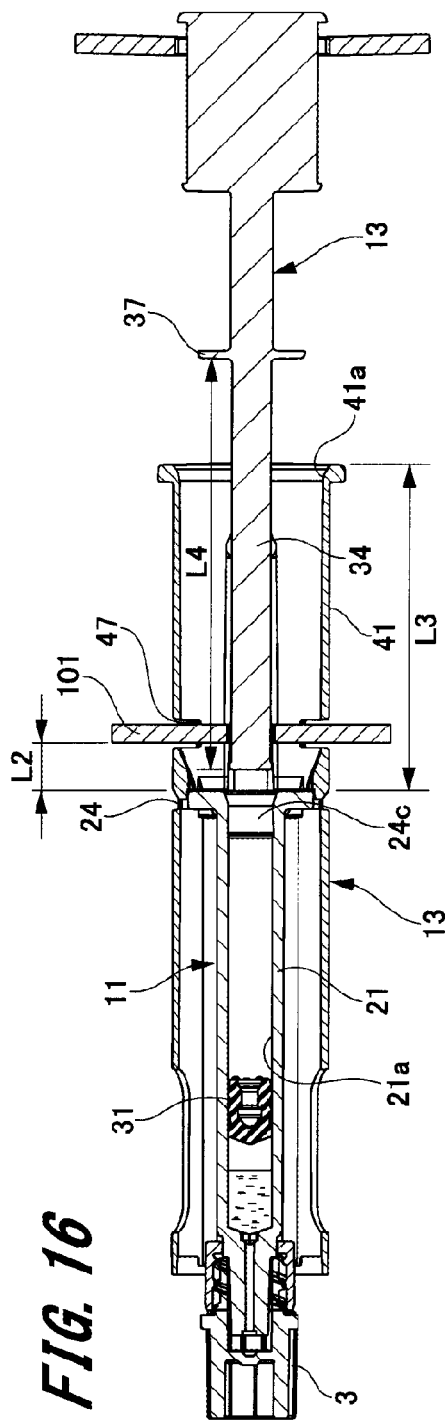
FIG. 16 is a cross-sectional view taken along the line G-G illustrated in FIG. 13.

As illustrated in FIGS. 14 to 16, the pair of guide members 101 is disposed so as to sandwich a distal end portion of the pusher body 34 inserted into the barrel body 41. At this time, the V-shaped guide grooves 101a formed at the end portions, facing the side surfaces of the pusher member 12 are brought into contact with the side surfaces of the distal end portion of the pusher body 34 so that it is possible to align the shaft center of the pusher body 34 with the center of the opening 24c of the syringe 11. Accordingly, it is possible to insert the pusher body 34 into the opening 24c of the syringe 11 without deviation.

Furthermore, as illustrated in FIG. 16, the insertion holes 47 into which the pair of guide members 101 is inserted are disposed close to the fixing claws 43 to fix the flange 24. Since the length L1 of the insertion holes 47 is larger than the outer diameter d1 of the pusher body 34, a width of the guide members 101 can be made larger than the outer diameter d1 of the pusher body 34. Accordingly, it is possible to reliably align the shaft center of the pusher body 34 with the center of the opening 24c of the syringe 11.

Furthermore, since the axial length L4 of the pusher body 34 is set within the range of 8 to 25 times the size of the outer diameter d1, the pusher body 34 is likely to bend at the time of handling. Therefore, as the shaft center of the bent pusher body 34 is corrected by the guide members 101 inserted from the insertion holes 47, it is possible to reliably insert the pusher body 34 into the opening 24c of the syringe 11.

The shape of the guide grooves 101a formed at the end portions of the guide members 101 facing the side surfaces of the pusher member 12 is not limited to the V-shape, but may be any other shapes such as a trapezoidal shape or an arc shape. Alternatively, the guide grooves 101a may not be provided to the distal end portions of the guide members 101.

Herein, it is preferable that a length L2 of the syringe 11 held by the syringe holder 13 which is from the insertion holes 47 to the opening 24c is set to, for example, a range of 1 to 10 mm. Accordingly, the guide members 101 inserted into the barrel body 41 from the insertion holes 47 can reliably guide the pusher body 34 to the opening 24c of the syringe 11 without interfering with the flange 24 of the syringe 11. Furthermore, when the syringe holder 13 is mounted on the syringe 11, a length L3 from the holder opening 41a of the barrel body 41 to the opening 24c of the syringe 11 is set to, for example, a range of 20 to 60 mm.

It is preferable that the length L2 is made as short as possible in order to inhibit deviation of the distal end portion of the pusher body 34 from the opening 24c. The length L3 is set to the range of 20 to 60 mm, and the operating portion 35 which is a proximal end portion of the pusher member 12 inserted into the syringe holder 13 is located in a side closer to the proximal end portion than the holder opening 41a so that an axial length of the pusher member 12 is longer than 20 to 60 mm. Therefore, the axial length of the pusher member 12 becomes longer than the pusher body 34 of the pusher member 12, which causes the pusher body 34 to bend easily at the time of handling. Therefore, as the shaft center of the bent pusher body 34 is corrected by the guide members 101 inserted from the insertion holes 47, it is possible to reliably insert the pusher body 34 into the opening 24c of the syringe 11.

Figure 17:
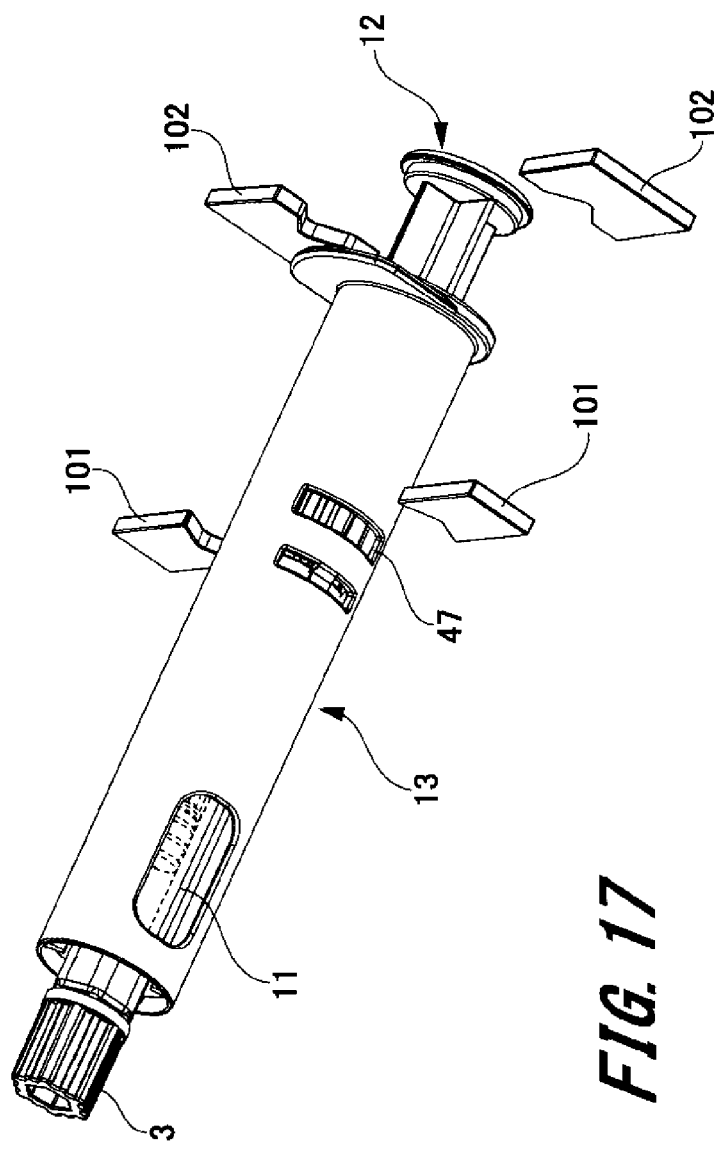
FIG. 17 is a perspective view illustrating a state after the pusher member being mounted on the pharmaceutical liquid administration device according to one embodiment.

Next, the pusher member 12 is further inserted into the cylindrical hole 21a of the body section 21 of the syringe 11. When the distal end portion in the axial direction of the pusher body 34 of the pusher member 12 is inserted into the opening 24c of the syringe 11, the guide members 101 are pulled out from the insertion holes 47. When the pusher member 12 is further inserted, and the pusher member 12 is inserted to a predetermined position as illustrated in FIG. 17, the chuck member 102 supporting the pusher member 12 is separated from the pusher member 12. Accordingly, the assembly of the pharmaceutical liquid administration device 1 is completed.

As described above, mounting the syringe holder 13 on the syringe 11 increases the diameter of the administration device body 2, which makes it easier to grasp the administration device body 2. Thus, the operability is improved at the time of operating the pusher member 12. According to the pharmaceutical liquid administration device 1 of this embodiment, it is possible to easily mount the syringe holder 13 on a commonly-used syringe without changing the shape of the syringe 11.

As illustrated in FIG. 2, when the injection needle assembly 90 is attached to the administration device body 2 as an administration component, the distal end portion of the administration device body 2, that is, the Luer Lock portion 26 of the syringe 11 is brought into contact with the injection needle assembly 90 stored in the storage case 93. Then, the female threaded portion 27a of the Luer Lock portion 26 and the male threaded portion 91 provided to the injection needle assembly 90 are screwed together. At this time, mounting the syringe holder 13 on the syringe 11 increases the diameter of the administration device body 2, which makes it easier to screw the injection needle assembly 90 and the syringe 11 together.

Furthermore, the outer diameter of the storage case 93 is set larger than the outer diameter of the flange 24 of the syringe 11. In screwing the injection needle assembly 90, the storage case 93 rotates together with the injection needle assembly 90 due to the engaged portion 93*a* engaged with the engaging portion 90*a* of the injection needle assembly 90. Therefore, when the injection needle assembly 90 is screwed, it is possible to increase not only the diameter of the injection needle assembly 90 but also the diameter of the administration device body 2, which makes it easier to screw the injection needle assembly 90 and the syringe 11 together.

Furthermore, in the administration device body 2 according to this embodiment, the radial movement-restricting portions 45 and the rotation restricting portions 44 are provided to the barrel body 41 of the syringe holder 13. Therefore, it is possible to inhibit the central axis of the syringe 11 from moving in the radial direction inside the cylindrical hole of the barrel body 41 due to rotational torque, and to inhibit the syringe 11 from rotating inside the cylindrical hole of the barrel body 41. Accordingly, it possible to inhibit the syringe holder 13 from spinning around, and to inhibit damage on of the fixing claws 43 of the syringe holder 13 due to the rotation of the syringe 11.

While certain embodiments are described above, the pharmaceutical liquid administration device of the present invention is not limited to the above embodiments, and can be variously modified without deviating from the gist of the invention recited in the claims.

It should be noted that the administration component to be mounted on the administration device body 2 of the pharmaceutical liquid administration device 1 is not limited to the aforementioned injection needle assembly 90. As an administration component to be mounted on the pharmaceutical liquid administration device 1, other various administration components may be applied as long as they can be mounted by screwing: for example, a needle-free syringe without a needle tube, an intranasal administration device for administering a pharmaceutical liquid to a nasal cavity.

In the aforementioned embodiment, the Luer Lock portion 26 is described as a screw portion, but the present invention is not limited thereto. A male threaded portion may be provided to the discharge portion 22, and a female threaded portion may be provided to the administration component so as to screw the both threaded portions.

Other configurations are described below.

In one embodiment, a syringe holder is configured to hold a syringe that comprises a body section having a cylindrical shape that is filled with a pharmaceutical liquid therein, a discharge portion formed at a distal end portion of the body section, an opening formed at a proximal end portion of the body section, and a gasket slidably disposed inside the body section, wherein the opening is a portion from which a pusher member is inserted into the body section, the pusher member including a pusher body that has a rod-like shape and is configured to slide the gasket in a distal end direction. The syringe holder includes: a barrel body having a cylindrical shape, and being configured to cover at least an outer peripheral surface of a proximal end portion of the syringe; a holder opening provided to a proximal end portion of the barrel body, the holder opening being configured for inserting the syringe; and an insertion hole penetrating a side wall of the barrel body, being provided close to the opening of the syringe held inside the barrel body and being provided in a side closer to the proximal end portion than the opening. The insertion hole is configured that a guide member is insertable into the barrel body through the insertion hole, the guide member being configured to be correctable a shaft center of the pusher body inserted into the barrel body from the holder opening.

In one aspect, the insertion hole is provided in a two or more at substantially equal intervals along a circumferential direction of the barrel body.

In one aspect, the syringe holder has a length set within a range of 1 to 10 mm from the insertion hole to the opening held inside the barrel body.

In one aspect, the syringe holder has a length set within a range of 20 to 60 mm from the opening of the syringe held inside the barrel body to the holder opening.

In one aspect, the holder opening is positioned distal of a proximal end portion of the pusher member inserted into the barrel body.

In one aspect, the insertion hole has a width in a direction orthogonal to an axial direction of the barrel body, the width being set larger than an outer diameter of the pusher body of the pusher member inserted into the body section.

In another aspect, a pharmaceutical liquid administration set includes: a syringe including a body section having a cylindrical shape that is filled with a pharmaceutical liquid therein, a discharge portion formed at a distal end portion of the body section, an opening formed at a proximal end portion of the body section, and a gasket slidably disposed inside the body section; a syringe holder configured to hold the syringe; and a pusher member being inserted into the body section from the opening, and including a pusher body that has a rod-like shape and is configured to slide the gasket in a distal end direction. The syringe holder includes: a barrel body having a cylindrical shape, being configured to cover at least an outer peripheral surface of a proximal end portion of the syringe; a holder opening provided to a proximal end portion of the barrel body, the holder opening being configured for inserting the syringe; and an insertion hole that penetrates a side wall of the barrel body, the insertion hole being provided close to the opening of the syringe held inside the barrel body and being provided in a side closer to the proximal end portion than the opening. The insertion hole is configured that a guide member is inserted thereinto, the guide member being configured to guide the pusher body, which inserted into the barrel body from the holder opening, to the opening of the syringe held inside the barrel body.

In one aspect, the pusher body has a length in an axial direction which is set within a range of 8 to 25 times the size of an outer diameter of the pusher body.

In another embodiment, a method for manufacturing a pharmaceutical liquid administration device includes: preparing a syringe that comprises a body section having a cylindrical shape that is filled with a pharmaceutical liquid therein, a discharge portion formed at a distal end portion of the body section, an opening formed at a proximal end portion of the body section, and a gasket slidably disposed inside the body section; holding the syringe in a syringe holder, the syringe holder including a barrel body that has a cylindrical shape and is configured to cover an outer peripheral surface of a proximal end portion of the syringe; preparing a pusher member including a pusher body that has a rod-like shape and is configured to slide the gasket in a distal end direction; inserting the pusher body into the barrel body from a holder opening provided to a proximal end portion of the barrel body; inserting a guide member from an insertion hole that penetrates a side wall of the barrel body, the insertion hole being provided close to the opening of the syringe held inside the barrel body and being provided in a side closer to the proximal end portion than the opening; guiding the pusher body to the opening by the guide member; and inserting the pusher body into the body section from the opening.

In one aspect, the method further includes: bringing the guide member into contact with a side surface of the pusher body inserted into the barrel body so as to align a shaft center of the pusher body with the center of the opening of the syringe held inside the barrel body, thereby guiding the pusher body to the opening.

In one aspect, the insertion hole is provided in a two or more at substantially equal intervals along a circumferential direction of the barrel body.

In one aspect, the guide member is provided with a substantially V-shaped guide groove provided to an end portion of the guide member facing a side surface of the pusher body.

According to the above configurations, it is possible to provide a method for manufacturing a syringe holder, a pharmaceutical liquid administration set, and a pharmaceutical liquid administration device in which a distal end of a pusher member can be inserted into an opening of a syringe without deviation when inserting the pusher member into the syringe.

Embodiments described herein can be applied to a syringe holder configured to hold a syringe having a distal end portion screwed with an administration component to administer a pharmaceutical liquid, and can be applied to a pharmaceutical liquid administration set provided with this syringe holder.

Embodiments described herein can also be applied to a method for manufacturing a syringe holder having a distal end portion into which an administration component is screwed, being provided to a pharmaceutical liquid administration device for administering a pharmaceutical liquid into a body, and for manufacturing a pharmaceutical liquid administration set provided with this syringe holder, and the pharmaceutical liquid administration device.

REFERENCE NUMERAL LIST

1 PHARMACEUTICAL LIQUID ADMINISTRATION DEVICE
2 ADMINISTRATION DEVICE BODY
3 CAP
10 PHARMACEUTICAL LIQUID ADMINISTRATION SET
11 SYRINGE
12 PUSHER MEMBER
13 SYRINGE HOLDER
21 BODY SECTION
21a CYLINDRICAL HOLE
22 DISCHARGE PORTION
23 LIQUID CHAMBER
24 FLANGE
24a FIRST PORTION
24b SECOND PORTION
24c OPENING
26 LUER LOCK PORTION (SCREW PORTION)
27a FEMALE THREADED PORTION (SCREW PORTION)
31 GASKET
34 PUSHER BODY
35 OPERATING PORTION
36 LOCK PORTION
37 FIRST COLLAR
37a ANTI-DROP PROJECTION
38 SECOND COLLAR
41 BARREL BODY
41a HOLDER OPENING
42 THROUGH HOLE (DEFORMATION PROMOTING PORTION)
43 FIXING CLAW
44 ROTATION RESTRICTING PORTION
44a CONTACT PROJECTION
45 RADIAL MOVEMENT-RESTRICTING PORTION
46 VIEWING WINDOW
47 INSERTION HOLE
48 HOLDER COLLAR
49 INCLINATION RESTRICTING RIB
51 FIXING PROJECTION
52 PROTUBERANT PORTION
54 RIB MEMBER
90 INJECTION NEEDLE ASSEMBLY (ADMINISTRATION COMPONENT)
90a ENGAGING PORTION
92 NEEDLE TUBE
93 STORAGE CASE
101 GUIDE MEMBER
101a GUIDE GROOVE
102 CHUCK MEMBER

What is claimed is:

1. A syringe holder configured to hold a syringe that comprises a cylindrical body section configured to be filled with a pharmaceutical liquid, a discharge portion formed at a distal end portion of the body section, a flange that is formed at a proximal end portion of the body section and includes a first portion disposed at a position a first distance apart from a central axis of the body section, and a second portion disposed at a position a second distance apart from the central axis, the second distance being smaller than the first distance, and a screw portion coupled to the discharge portion and configured to be screwed to an administration component to administer the pharmaceutical liquid to a biological body, the syringe holder comprising:

a barrel body having a cylindrical shape and being configured to cover at least an outer peripheral surface of the flange of the syringe;

a holder opening defined by the barrel body, the holder opening being configured for inserting the syringe;

a fixing claw configured to fix a surface of the flange on a side proximate the holder opening;

a fixing projection configured to fix a surface of the flange on a side opposite to the holder opening;

a through hole that penetrates a side wall of the barrel body and is located proximate an end portion of the fixing claw on a side opposite to the holder opening, the through hole being configured to promote the fixing claw to deform outward in a radial direction of the barrel body when the first portion of the syringe inserted from the holder opening climbs over the fixing claw;

a rotation restricting portion configured to come into contact with the second portion so as to restrict the syringe from rotating in a circumferential direction with respect to the barrel body; and projection that closes a part of the through hole, the projection being configured to come into contact with the first portion so as to restrict the syringe from moving in the radial direction with respect to the barrel body, wherein the projection connects a distal end of the through hole and a proximal end of the through hole such that a distal end portion of the projection is thinner than a proximal end portion of the projection that is configured to contact the long diameter portion.

2. The syringe holder according to claim 1, wherein the through hole has a length in a circumferential direction in a range of 15 to 35% of an outer peripheral length of the barrel body.

3. The syringe holder according to claim 1, wherein the second portion comprises a pair of second portions that face each other across the central axis, and wherein the rotation restricting portion comprises a pair of rotation restricting portions that face each other, each rotation restriction portion being configured to come into contact with a respective one of the pair of second portions.

4. The syringe holder according to claim 1, wherein the rotation restricting portion comprises a rib protruding from an inner peripheral surface of the barrel body.

5. The syringe holder according to claim 1, wherein the second portion comprises a pair of second portions that face each other across the central axis, and wherein the rotation restricting portion comprises two pairs of ribs, each pair of ribs being configured to come into contact with a respective one of the pair of second portions.

6. The syringe holder according to claim 1, wherein, when the barrel body holds the syringe, the barrel body has a length in a range of 20 to 60 mm from the holder opening to the flange of the syringe, and wherein the rotation restricting portion extends to a vicinity of the holder opening.

7. The syringe holder according to claim 1, wherein an outer diameter of the barrel body is larger than an outer diameter of the flange.

8. The syringe holder according to claim 1, wherein the syringe comprises:
an opening formed at the proximal end portion of the body section, and
a gasket slidably disposed inside the body section,
wherein the opening of the syringe is a portion from which a pusher member is insertable into the body section, the pusher member including a pusher body that has a rod-like shape and is configured to slide the gasket in a distal end direction, and
wherein the syringe holder comprises an insertion hole that penetrates a side wall of the barrel body, the insertion hole being provided proximate the opening of the syringe held inside the barrel body and being provided on a side closer to the proximal end portion than the opening,
wherein the insertion hole is configured such that a guide member is insertable into the barrel body through the insertion hole, the guide member being configured to correct a shaft center of the pusher body that is inserted into the barrel body from the holder opening.

9. A pharmaceutical liquid administration set comprising:
a syringe that comprises:
a cylindrical body section configured to be filled with a pharmaceutical liquid,
a discharge portion formed at a distal end portion of the body section,
a flange that is formed at a proximal end portion of the body section and includes a first portion extending a first distance from a central axis of the body section, and a second portion extending a second distance from the central axis, the second distance being smaller than the first distance, and
a screw portion coupled to the discharge portion and configured to be screwed to an administration component to administer the pharmaceutical liquid to a biological body; and
a syringe holder comprising:
a barrel body having a cylindrical shape and being configured to cover at least an outer peripheral surface of the flange of the syringe,
a holder opening defined by the barrel body, the holder opening being configured for inserting the syringe,
a fixing claw configured to fix a surface of the flange on a side proximate the holder opening,
a fixing projection configured to fix a surface of the flange on a side opposite to the holder opening,
a through hole that penetrates a side wall of the barrel body and is located proximate an end portion of the fixing claw on a side opposite to the holder opening, the through hole being configure to promote the fixing claw to deform outward in a radial direction of the barrel body when the first portion of the syringe inserted from the holder opening climbs over the fixing claw,
a rotation restricting portion configured to come into contact with the second portion so as to restrict the syringe from rotating in a circumferential direction with respect to the barrel body, and
a through hole, the projection being configured to come into contact with the first portion so as to restrict the syringe from moving in the radial direction with respect to the barrel body,
wherein the projection extends in a direction opposite to the holder opening from the end portion of the fixing claw in the side opposite to the holder opening, and
wherein the projection extends part way in an axial direction of the through hole, the projection having a free end portion on the side opposite to the holder opening.

10. The pharmaceutical liquid administration set according to claim 9, wherein the syringe further comprises:
an opening formed at the proximal end portion of the body section, and
a gasket slidably disposed inside the body section, and
wherein the pharmaceutical liquid administration set further includes a pusher member inserted into the body section from the opening, the pusher member comprising a pusher body that has a rod-like shape and is configured to slide the gasket in a distal end direction,
wherein the syringe holder further comprises an insertion hole that penetrates a side wall of the barrel body, the insertion hole being provided proximate the opening of the syringe held inside the barrel body and being provided on a side closer to the proximal end portion than the opening,
wherein the insertion hole is configured such that a guide member is insertable into the barrel body through the insertion hole, the guide member being configured to correct a shaft center of the pusher body that is inserted into the barrel body from the holder opening.

11. The pharmaceutical liquid administration set according to claim 9, further comprising:
an administration component that comprises a screw portion that is configured to be screwed together with the screw portion of the syringe, the administration component being attachable to the syringe; and a cylindrical storage case, the storage case being configured to store the administration component, wherein the administration component comprises a first engaging portion, and the storage case comprises a second engaging portion that is engaged with the first engaging portion so as to rotate the administration component together with the storage case, and wherein the screw portion and the screwed portion are configured to be screwed together by a rotation of the storage case relative to the syringe.

12. The pharmaceutical liquid administration set according to claim 11,
wherein the storage case has an outer diameter in a range of 10 to 30 mm.

13. A syringe holder configured to hold a syringe that comprises a cylindrical body section configured to be filled with a pharmaceutical liquid, a discharge portion formed at a distal end portion of the body section, a flange that is formed at a proximal end portion of the body section and includes a first portion disposed at a position a first distance apart from a central axis of the body section, and a second portion disposed at a position a second distance apart from the central axis, the second distance being smaller than the first distance, and a screw portion coupled to the discharge portion and configured to be screwed to an administration component to administer the pharmaceutical liquid to a biological body, the syringe holder comprising:

a barrel body having a cylindrical shape and being configured to cover at least an outer peripheral surface of the flange of the syringe;

a holder opening defined by the barrel body, the holder opening being configured for inserting the syringe;

a fixing claw configured to fix a surface of the flange on a side proximate the holder opening;

a fixing projection configured to fix a surface of the flange on a side opposite to the holder opening;

a through hole that penetrates a side wall of the barrel body and is located proximate an end portion of the fixing claw on a side opposite to the holder opening, the through hole being configured to promote the fixing claw to deform outward in a radial direction of the barrel body when the first portion of the syringe inserted from the holder opening climbs over the fixing claw;

a rotation restricting portion configured to come into contact with the second portion so as to restrict the syringe from rotating in a circumferential direction with respect to the barrel body; and a projection that closes a part of the through hole, the projection being configured to come into contact with the first portion so as to restrict the syringe from moving in the radial direction with respect to the barrel body, wherein the projection extends in a direction opposite to the holder opening from the end portion of the fixing claw in the side opposite to the holder opening, and wherein the projection extends part way in an axial direction of the through hole, the projection having a free end portion on the side opposite to the holder opening.

14. The syringe holder according to claim 13,
wherein the through hole has a length in a circumferential direction in a range of 15 to 35% of an outer peripheral length of the barrel body.

15. The syringe holder according to claim 13,
wherein the second portion comprises a pair of second portions that face each other across the central axis, and
wherein the rotation restricting portion comprises a pair of rotation restricting portions that face each other, each rotation restriction portion being configured to come into contact with a respective one of the pair of second portions.

16. The syringe holder according to claim 13,
wherein the rotation restricting portion comprises a rib protruding from an inner peripheral surface of the barrel body.

17. The syringe holder according to claim 13,
wherein the second portion comprises a pair of second portions that face each other across the central axis, and
wherein the rotation restricting portion comprises two pairs of ribs, each pair of ribs being configured to come into contact with a respective one of the pair of second portions.

18. The syringe holder according to claim 13,
wherein, when the barrel body holds the syringe, the barrel body has a length in a range of 20 to 60 mm from the holder opening to the flange of the syringe, and
wherein the rotation restricting portion extends to a vicinity of the holder opening.

19. The syringe holder according to claim 13,
wherein an outer diameter of the barrel body is larger than an outer diameter of the flange.

20. The syringe holder according to claim 13,
wherein the syringe comprises:
an opening formed at the proximal end portion of the body section, and
a gasket slidably disposed inside the body section,
wherein the opening of the syringe is a portion from which a pusher member is insertable into the body section, the pusher member including a pusher body that has a rod-like shape and is configured to slide the gasket in a distal end direction, and
wherein the syringe holder comprises an insertion hole that penetrates a side wall of the barrel body, the insertion hole being provided proximate the opening of the syringe held inside the barrel body and being provided on a side closer to the proximal end portion than the opening,
wherein the insertion hole is configured such that a guide member is insertable into the barrel body through the insertion hole, the guide member being configured to correct a shaft center of the pusher body that is inserted into the barrel body from the holder opening.

* * * * *